(12) United States Patent
Higuchi et al.

(10) Patent No.: US 6,489,987 B1
(45) Date of Patent: Dec. 3, 2002

(54) ELECTRONIC ENDOSCOPE APPARATUS

(75) Inventors: Mitsuru Higuchi, Omiya (JP);
Kazuhiro Yamanaka, Omiya (JP)

(73) Assignee: Fuji Photo Optical Co., Ltd., Saitama (JP)

( * ) Notice: Subject to any disclaimer, the term of this patent is extended or adjusted under 35 U.S.C. 154(b) by 0 days.

(21) Appl. No.: 09/225,204

(22) Filed: Jan. 4, 1999

(30) Foreign Application Priority Data

| Jan. 9, 1998 | (JP) | 10-014980 |
| Jan. 30, 1998 | (JP) | 10-033776 |
| Jan. 30, 1998 | (JP) | 10-033777 |
| Feb. 4, 1998 | (JP) | 10-038170 |
| Feb. 4, 1998 | (JP) | 10-038171 |
| Feb. 18, 1998 | (JP) | 10-054421 |

(51) Int. Cl.[7] .................................... H04N 7/18
(52) U.S. Cl. ......................................... 348/65
(58) Field of Search .......................... 348/65, 68–71; 600/101, 109, 160, 178, 180; H04N 7/18

(56) References Cited

U.S. PATENT DOCUMENTS

| 4,803,550 A | * | 2/1989 | Yabe et al. ............... 600/109 |
| 4,866,516 A | * | 9/1989 | Hibino et al. ............... 348/68 |
| 4,869,256 A | * | 9/1989 | Kanno et al. ............... 600/109 |
| 5,010,395 A | * | 4/1991 | Tsuji et al. ............... 348/71 |
| 5,034,888 A | * | 7/1991 | Uehara et al. ............... 600/101 |
| 5,387,928 A | * | 2/1995 | Nishimura ............... 348/70 |
| 5,929,900 A | * | 7/1999 | Yamanaka et al. ............... 348/65 |
| 6,002,425 A | * | 12/1999 | Yamanaka et al. ............... 348/68 |
| 6,234,959 B1 | * | 5/2001 | Higuchi et al. ............... 600/180 |

* cited by examiner

Primary Examiner—Richard Lee
(74) Attorney, Agent, or Firm—Snider & Associates; Ronald R. Snider

(57) ABSTRACT

This electronic endoscope apparatus is capable of forming a still image with high image quality by reading out all pixels obtained through an image-pickup device by one exposure and faithfully reproducing the movement concerning moving images. A switch between a pixel mix reading system, which mixes pixels accumulated on the image pickup device having a plurality of color filters arranged in units of pixels between upper and lower horizontal lines to read out from the image-pickup device, and an all-pixel reading system, which reads out signals of all pixels accumulated on the image-pickup device by one exposure uses a light shielding period set by a light shielded. This all-pixel reading system forms a still image, and the other pixel mix reading system forms a moving image. Also, moving image data are delayed using a delay memory, and still image data are prevented from being written in a memory as moving image data, whereby display of any incomplete image is prevented on switching the moving image to the still image. Further, black level voltage in a moving image signal will always be used even when the still image is selected.

7 Claims, 15 Drawing Sheets

ODD-line 23 (25)

EVEN-line 24

(C1)

OUTPUT FROM MIXING CIRC.

(Odd Field)

OUTPUT FROM MIXING CIRC.

(Even Field)

FIG.12(A) MOVING IMAGE SIGNAL 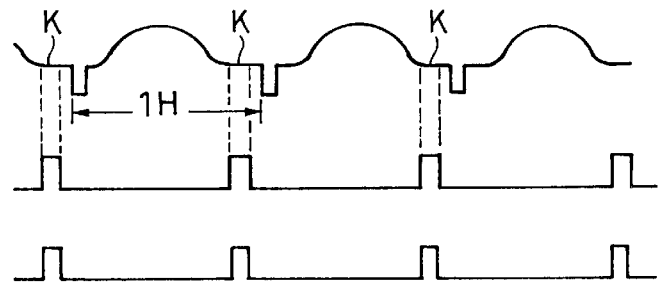
FIG.12(B) O B P 
FIG.12(C) CLAMP PULSE 
FIG.13(A) STILL IMAGE SIGNAL 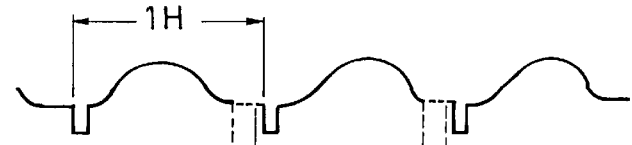
FIG.13(B) MOVING IMAGE SIGNAL
FIG.13(C) SWITCHING SIGNAL 
FIG.13(D) O B P 
FIG.13(E) CLAMP PULSE 

FIG.16
PRIOR ART
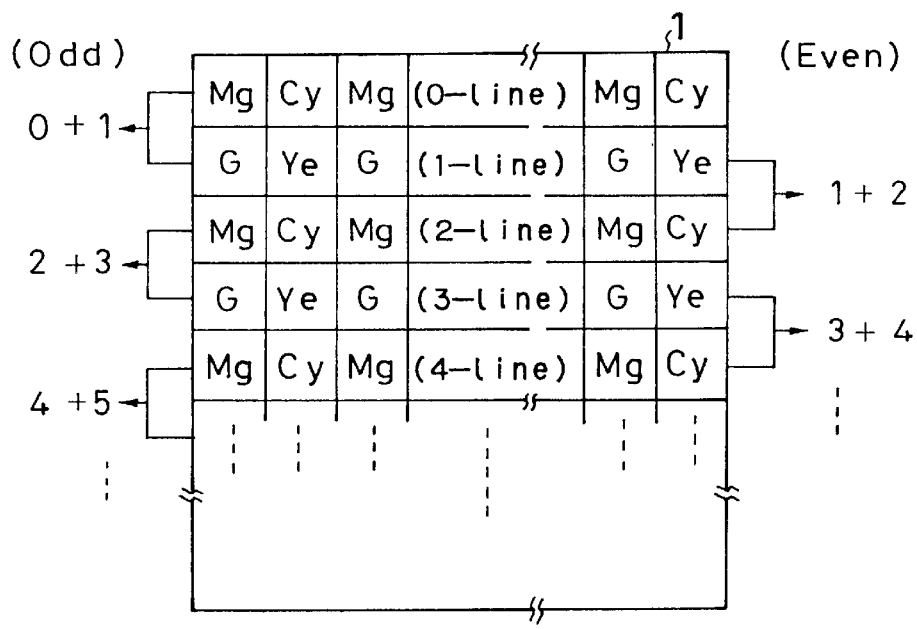
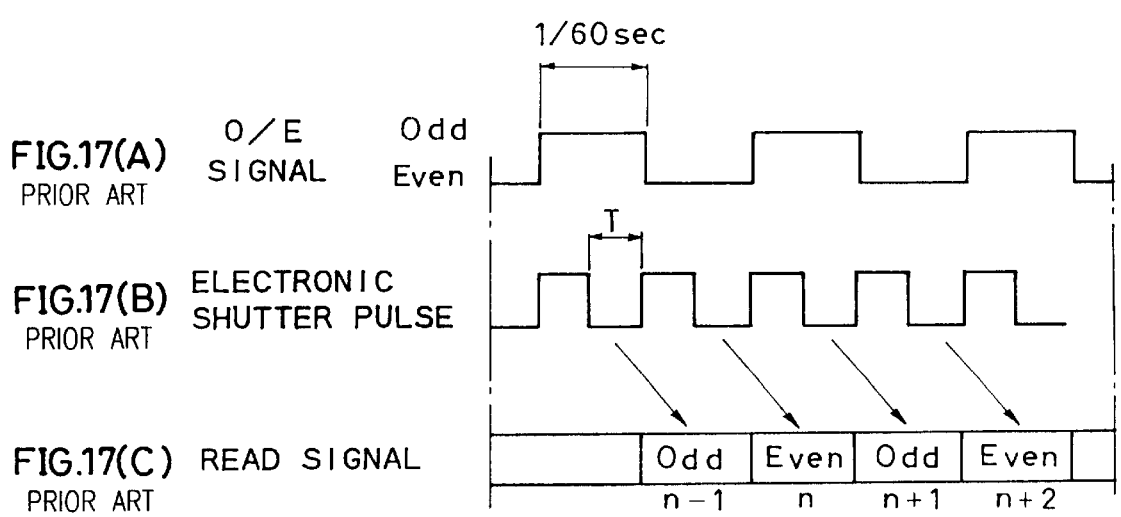
FIG.17(A) PRIOR ART O/E SIGNAL
FIG.17(B) PRIOR ART ELECTRONIC SHUTTER PULSE
FIG.17(C) PRIOR ART READ SIGNAL

ELECTRONIC ENDOSCOPE APPARATUS

BACKGROUND OF THE INVENTION

This application claims the priority of Japanese Patent Application No. 10-14980 filed on Jan. 9, 1998, Nos. 10-33776 and 10-33777 filed on Jan. 30, 1998, Nos. 10-38170 and 10-38171 filed on Feb. 4, 1998 and No. 10-54421 filed on Feb. 18, 1998 which are incorporated herein by reference.

The present invention relates to an electronic endoscope apparatus, and more particularly to structure of an electronic endoscope apparatus for forming a still image through the use of an all-pixel reading system which reads out all pixels accumulated on an image-pickup device.

DESCRIPTION OF THE PRIOR ART

In an electronic endoscope apparatus, for example, CCD (Charge Coupled Device) is used as a solid image-pickup device, and this CCD is structured so as to obtain an image signal (video signal) by reading out charge accumulated in units of pixels by a photoelectric conversion device. In, for example, a simultaneous type electronic endoscope apparatus, color filters are arranged in units of pixels on the top surface of the foregoing CCD to thereby obtain a color image.

FIG. 16 shows an arrangement state for the foregoing color filters, and Mg (magenta) and Cy (cyan) pixels are arranged on, for example, an even line, and G (green) and Ye (yellow) pixels are arranged on an odd line on a picked-up surface of CCD 1 as shown. In this CCD 1, accumulated charge (pixel signal) in units of pixels is to be obtained through these color filters.

According to a conventional color difference line sequential mix reading (pixel mix reading) system, accumulated charges of pixels on the upper and lower lines are added and mixed to be read out. For example, during first exposure, video signals of such Odd field as a mixed signal of 0-line and 1-line, a mixed signal of 2-line and 3-line, . . . are read out, and during the second exposure, video signals of such even field as a mixed signal of 1-line and 2-line, a mixed signal of 3-line and 4-line, . . . are read out. Therefore, two lines of mixed signals of CCD 1 become one line of signals of field image, and one odd or even field of data are to be obtained by one exposure.

FIG. 17 shows an operation of signals read out from the foregoing CCD 1, and in an electronic endoscope apparatus, an odd field and an even field are formed on the basis of the O (Odd)/E (Even) signal (field signal) for each ⅟₆₀ second (vertical synchronizing period) as shown in FIG. 17(A). Therefore, as shown in FIG. 17(B), signals are accumulated in accumulation (exposure) time T of an electronic shutter during the foregoing period of ⅟₆₀ second, and the accumulation mixed signal is read out during the next ⅟₆₀ second period. As a result, as shown in FIG. 17(C), an odd field signal, and an even field signal are to be obtained, and for example, the (n−1)th odd field signal becomes mixed signals of (0+1)line, (2+3)line, (4+5)line . . . which are shown on the left of FIG. 16, and the n-th even field signal becomes mixed signals of (1+2)line, (3+4)line, . . . which are shown on the right of FIG. 16.

These odd field signals and even field signals are interlace scanned to be formed as an one-frame image, and this image is displayed as a moving image on a monitor. Also, in the endoscope apparatus, a freeze switch is arranged in the operating unit, and when this freeze switch is depressed, a still image at the time is formed and displayed.

BRIEF SUMMARY OF THE INVENTION

In the foregoing simultaneous type electronic endoscope apparatus, however, there is a time lag of ⅟₆₀ second between those odd field image and even field image which are used to form the one-frame image as shown in the foregoing FIG. 17(C), and if there is a shake of the endoscope itself, a movement of the object to be observed or the like during this period of time, there is the problem that the image quality (resolution, color shift, etc.) will be deteriorated when the still image is displayed. In other words, in the case of a moving image, it is often better to faithfully reproduce the movement and the like of the subject conversely by the foregoing mix reading system in the CCD 1, but in the case of a still image, the resolution will be deteriorated.

Also, in the electronic endoscope apparatus, an electronic shutter function for changing the accumulation time of a signal is frequently adopted, and by the use of the electronic shutter, it is possible to improve the image quality if the accumulation time is made shorter in a light place at a short distance or the like. As shown in FIG. 17, however, there is a time lag of ⅟₆₀ second between two accumulation (exposure) for forming an one-frame image, and in a still image, there is the inconvenience that the effect of shortened accumulation time is not sufficiently exhibited.

The present invention has been achieved in the light of the foregoing problems, and is aimed to supply an electronic endoscope apparatus capable of forming a still image with high image quality by reading out all pixels obtained through an image-pickup device by one exposure, and faithfully reproducing the movement concerning a moving image.

Another object is to prevent, in the foregoing electronic endoscope apparatus, any incomplete image from being displayed or the screen from being blurred when switching from a moving image to a still image.

Still another object is to stabilize, in the foregoing electronic endoscope apparatus, black level clamping treatment when a still image is selected, and to prevent the image quality from being deteriorated.

SUMMARY OF THE INVENTION

In order to achieve the foregoing object, an electronic endoscope apparatus according to a first invention comprises: an image-pickup device having a plurality of color filters arranged in units of pixels; light shielding means for intercepting illumination light so that pixel signals for a predetermined period of time are not accumulated on this image-pickup device; and switching means for switching driving control for both a pixel mix reading system, which mixes pixels accumulated on the foregoing image-pickup device between upper and lower horizontal lines to output from the image-pickup device, and a all-pixel reading system, which reads out signals of all pixels accumulated on the foregoing image-pickup device by one exposure through the use of a light shielding period set by the foregoing light shielding means.

In the foregoing, there can be provided control means for forming a moving image using the foregoing pixel mix reading system and a still image using the foregoing all-pixel reading system while controlling the foregoing switching means.

Also, the foregoing first invention is preferably structured by including: an image-pickup device driving circuit for controlling so as to read out, concerning all pixel signals accumulated on the foregoing image-pickup device by one exposure, image signals on either an odd line or an even line first, and next to read out image signals on the remaining line; a memory for storing, at the execution of the foregoing all-pixel reading system, image signals on the foregoing odd line obtained from the image-pickup device and image signals on the foregoing even line; a phase adjustment memory for adjusting phase, at the execution of the foregoing all-pixel reading system, between image signals on a predetermined line previously stored in the foregoing memory and image signals on the other line; a mixing circuit for forming a still image signal by mixing pixel signals of the foregoing odd line and the foregoing even line during the same exposure which have been read out from the foregoing each memory; and an image switching circuit for directly inputting a moving image signal of the pixel mix reading system outputted from the foregoing image-pickup device to switch either this moving image signal or the still image signal outputted from the foregoing mixing circuit on the basis of the operation of a freeze switch.

According to the foregoing structure, the pixel mix reading system has been selected at the output of the image-pickup device, during, for example, a normal operation, a pixel mixed signal read out from the image-pickup device in the same manner as before is directly supplied to the image switching circuit, and a pixel mixed signal outputted through this image switching circuit is subjected to the signal processing for a moving image. Thus, when the freeze switch is depressed, it is switched to the all-pixel reading system to thereby form a still image.

As regards, for example, charge accumulated by exposure (arbitrary exposure time) within a predetermined (assumed to be a first one) $1/60$ second period (vertical synchronizing period), the odd line of the image-pickup device (CCD) is read out during the second period ($1/60$ second) (read out from the transfer line) to be stored in a predetermined memory, and the remaining even line is read out during the third (next exposure time) period to be also stored in a predetermined memory. In order to enable this even line to be read out, the light source light during the foregoing second period is intercepted by the light shielding means.

In other words, when charge for the next exposure is accumulated as before during the second period in which the accumulated charge on the foregoing odd line is successively read out, the remaining even line cannot be read out. Therefore, according to the present invention, the light output within the second period is left out to read out accumulated charge on the even line during the third period. Thus, the signals for all pixels of the image-pickup device obtained by one exposure can be read out.

Next, a video signal on, for example, the odd line first stored in the foregoing memory is further stored in the phase adjustment memory, delayed by $1/60$ second, and thereafter, a pixel mixing process is performed between odd line data and even line data by the mixing circuit. More specifically, as a result, this pixel mixing process forms a similar signal to the pixel mix reading system at the output of an image-pickup device which is performed at the output of a signal from the image-pickup device, but is distinguished from pixel mix reading system at the output of an image-pickup device in terms of pixel mixing in accordance with the information obtained by one exposure.

Thus, this pixel mixing signal forms video signals for the odd field and the even field, and a still image is displayed on the basis of these video signals. Accordingly, the still image is to be formed on the basis of signals of all pixels obtained by one exposure, thus becoming a high-quality image.

An electronic endoscope apparatus according to a second invention is constituted by including, in the foregoing first invention, delay means for delaying moving image data obtained by the foregoing pixel mix reading system by a predetermined period, and a signal processing circuit for forming a moving image signal on the basis of moving image data obtained through this delay means.

This second invention eliminates the inconvenience which occurs when the operation described in the first invention is performed. More specifically, during a normal operation in which the freeze switch is not depressed, the pixel mix reading system at the output of an image-pickup device has been selected, and pixels of two horizontal lines read out from the image-pickup device are mixed and outputted in the same manner as before. On switching from the moving image to a still image, however, since the illumination light is intercepted, and it is switched to the all-pixel reading system, image processing is performed through moving image data which are a half the ordinary one in, for example, one frame immediately before the still image is displayed, thus causing such a phenomenon that an incomplete image (image having half luminance and improper color) is displayed. Thus, according to the second invention, the moving image data are delayed as a whole by processing time corresponding to one frame using, for example, the foregoing delay memory in such a manner that any moving image is not formed through image data obtained during intercepted light. In this way, the display of any improper image caused on switching from the moving image to a still image is prevented.

A third invention comprises: control means for forming a moving image using the foregoing pixel mix reading system and a still image using the foregoing all-pixel reading system; and a memory for storing at least the foregoing moving image data, and the foregoing control means inhibits still image data read out from the foregoing image-pickup device when the foregoing all-pixel reading system is selected from being written in the foregoing memory as moving image data. In other words, a write-inhibit signal is outputted to a memory, in which, for example, moving image data are stored, for controlling so that the still image data obtained using the all-pixel reading system are prevented from being written in the foregoing memory as moving image data. According to this invention, the immediately preceding moving image data already obtained are used again in place of the incomplete data, and the display of an improper image caused on switching to the still image is prevented as in the case of the foregoing second invention.

A fourth invention comprises: control means for forming a moving image using the foregoing pixel mix reading system and a still image using the foregoing all-pixel reading system; and a memory for storing at least the foregoing moving image data, and the foregoing control means sets a write-inhibit period to prevent still image data read out from the foregoing image-pickup device when the foregoing all-pixel reading system is selected from being written in the foregoing memory as moving image data. The foregoing control means also continuously reads out the data in either the odd field or the even field which have been already written in the memory as frame data during the foregoing write inhibit period.

This fourth invention controls, as in the case of the foregoing third invention, so as not to write still image data obtained using the all-pixel reading system in a memory in which moving image data are stored, and continuously reads out, for example, only odd field data. This prevents the display of any improper image caused on switching to a still image, and odd (or even) field data are continuously read out at least twice (for one frame), whereby blurring of an image can be suppressed. More specifically, as data for substituting as the still image data, the immediately preceding data can be also used again for both odd field and even field, but in this case, the image is displayed through data which are temporally inverted, and therefore, the display screen will be blurred if, for example, the object moves from side to side. Thus, according to the invention, the field data which are temporally inverted are not used, but only either odd or even data are read out to display the image for eliminating the blurred screen.

A fifth invention has the foregoing image-pickup device, light shielding means, and switching means for switching driving control for both systems, and comprises: a clamping circuit for clamping an image signal outputted from the foregoing image-pickup device through a clamp signal; switching control means for controlling so as to extract a black information signal in the moving image signal obtained by the pixel mix reading system at the output of the foregoing image-pickup device even when the foregoing all-pixel reading system is selected; and a signal processing circuit for forming a clamp signal from the black information signal obtained by the control of this switching control means to feed back this clamp signal to the foregoing clamping circuit.

Generally, in the image processing in an electronic endoscope apparatus, a clamping process for causing black levels to coincide for each horizontal scanning period is performed as well known, but in the clamping process for the foregoing still image (all-pixel reading system), since the displaying process is performed through image data once stored in the memory, the clamp signal is formed on the basis of old data. Therefore, during shifting from the still image to the moving image, the black level of the signal is greatly changed, and in this case, the reproducibility of color is deteriorated. In the fifth invention, however, a black information signal of the current moving image signal is extracted even when a still image is being processed for display, and a clamp signal is formed on the basis of this black information signal for clamping process. Therefore, the great fluctuation of the black level will be eliminated, and it becomes possible to display a good image even when the display is switched from a still image to a moving image.

An electronic endoscope apparatus according to a sixth invention has, as in the foregoing second invention, delay means for delaying moving image data obtained by the foregoing pixel mix reading system by a predetermined period, and is characterized by comprising switching control means for directly inputting a moving image signal obtained by the foregoing pixel mix reading system without passing through the foregoing delay means, and controlling so as to extract a black information signal in the moving image signal.

In the foregoing second invention, the moving image data are delayed as a whole by processing time corresponding to one frame by means of the delay memory so as to prevent any moving image from being formed through the image data obtained when light is intercepted. In the clamping process for the moving image in this case, however, the image data which have been stored once in the delay memory are used for display processing, and therefore, the black level will be determined on the basis of the old data although the same is applicable to the still image. Thus, according to the invention, apart from a processing signal for the moving image (or still image), the black information signal in the current moving image signal directly outputted from the image-pickup device is extracted to perform the clamping process on the basis of the black information signal. Therefore, the great fluctuation of the black level due to time lag is eliminated, and it becomes possible to display a good image when the moving image is selected or even when the display is switched from the still image to the moving image.

BRIEF DESCRIPTION OF THE DRAWINGS

FIGS. 12(A) to 12(C) are waveform views showing a clamping process when a moving image is selected in the fifth embodiment;

FIGS. 13(A) to 13(E) are waveform views showing a clamping process when a still image is selected in the fifth embodiment;

FIG. 16 is an explanatory view for illustrating structure of color filters and pixel mix reading in a conventional CCD; and FIGS. 17(A) to 17(C) are explanatory views for illustrating the operation in the conventional CCD.

DETAILED DESCRIPTION OF THE PREFERRED EMBODIMENTS

First Embodiment

Figure 1:
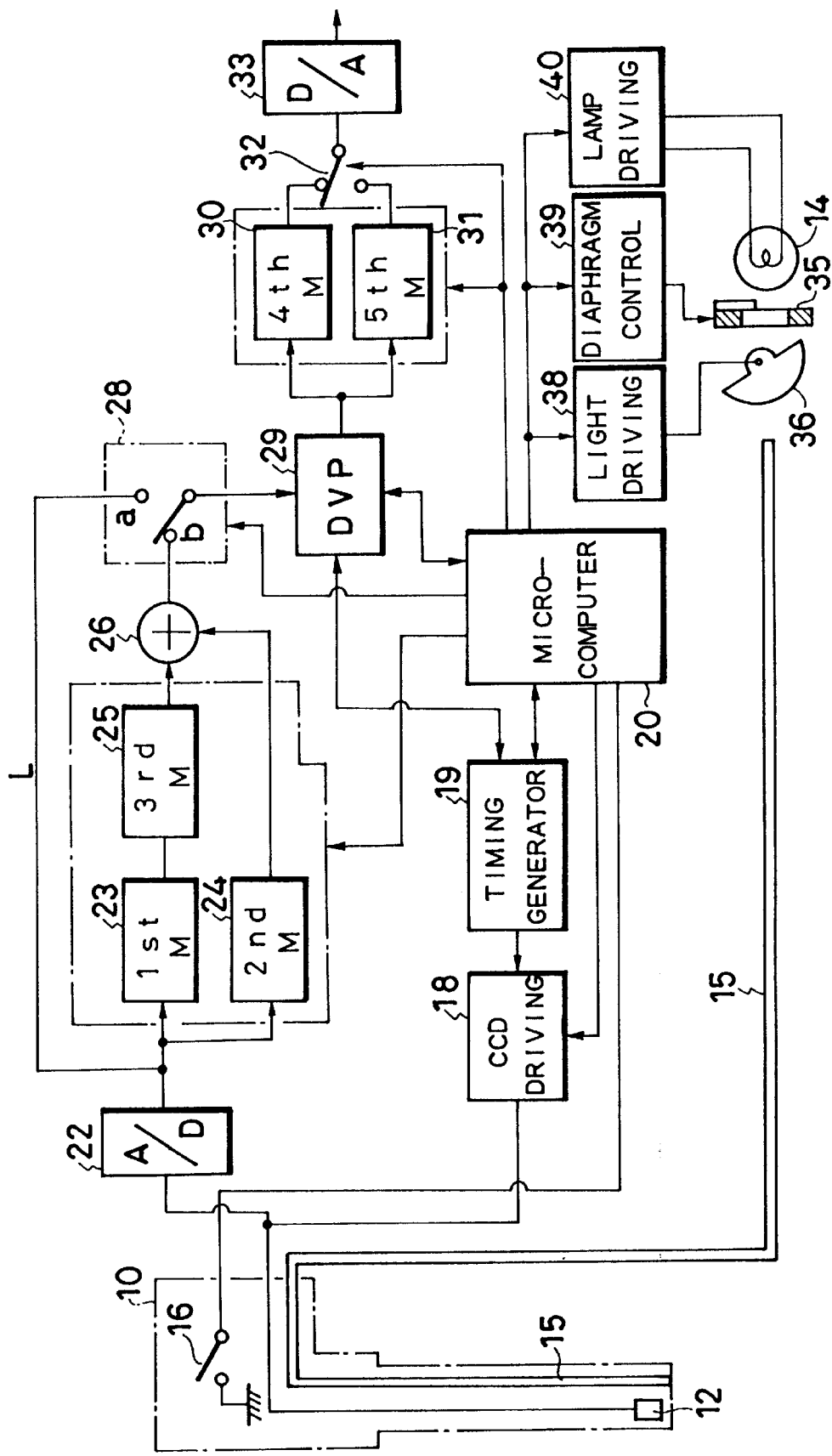
FIG. 1 is a block diagram showing a circuit configuration of an electronic endoscope apparatus according to a first embodiment of the present invention.

FIG. 1 shows a circuit configuration of an electronic endoscope apparatus as an example of embodiment, and this electronic endoscope apparatus has such structure that a scope (electronic endoscope) 10 is connected to a processor device having an image processing circuit or a light source device (or apparatus obtained by making these devices integral) having a light source. This scope 10 is provided with CCD 12 at whose tip end portion the same color filters as described in FIG. 16 are arranged, and with a light guide 15 for guiding light from the light source 14 to the tip end portion. Also, an operating unit for the scope 10 is provided with a freeze switch 16 for displaying a still image.

To the foregoing CCD 12, a CCD driving circuit 18 for driving it is connected, and to the driving circuit 18, there are connected a timing generator 19 and a microcomputer 20. To this microcomputer 20, an operation signal from the foregoing freeze switch 16 is inputted. The foregoing CCD driving circuit 18 inputs a timing signal under the control of the microcomputer 20 to control the driving of the pixel mix reading system at the output of CCD for moving images and the all-pixel reading system for still images.

In the case of, for example, the all-pixel reading system, two types of pulses for dividing accumulated data for all pixels, which have been accumulated in CCD 12 by one exposure, into the odd line and the even line (staggering also temporally) for reading out, are supplied from the foregoing CCD driving circuit 18, and on the basis of these pulses, control is performed so as to read out the foregoing odd line signals and even line signals from the CCD 12 separately and successively. In this respect, one type read pulse is imparted to each line in the pixel mix reading system at the output of CCD.

Also, there is provided an A-D converter 22 for inputting an output signal from the foregoing CCD 12, and at the subsequent stage of the A-D converter 22, there are provided a first memory 23 for storing image data of the foregoing odd line in order to read out all pixels, a second memory 24 for storing image data of the even line, a third memory 25 for phase adjustment for storing the data of the foregoing first memory 23 as they are and delaying the read timing by $\frac{1}{60}$ second, and a mixing circuit for still image 26. More specifically, all pixel signals obtained at the CCD 12 are divided into data (video signal) of the odd line and data of the even line, and in this state, are once stored in the respective memories 23 and 24, but the odd line data of the first memory 23 are caused to be delayed by $\frac{1}{60}$ second, whereby they are caused to have the same phase as the even line data stored in the second memory 24.

Thus, it becomes possible to read out both image data simultaneously, and in a mixing circuit 26 in the next stage, pixel data of the odd line in the third memory 25 and those of the even line in the second memory 24 can be added and mixed (pixel mixing process for still images). Therefore, in the case of still images, the same pixel mixed signal can be formed as the conventional pixel mix reading system by this mixing circuit 26.

Figure 2:
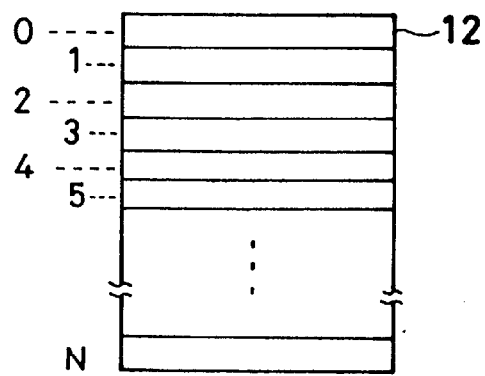
FIGS. 2(A) to 2(E) are views showing image data read out between CCD of FIG. 1 and the mixing circuit.
Figure 2:
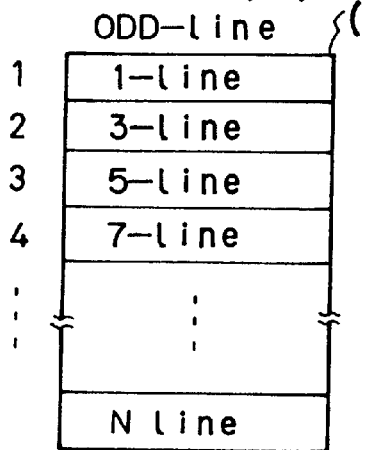
Figure 2:
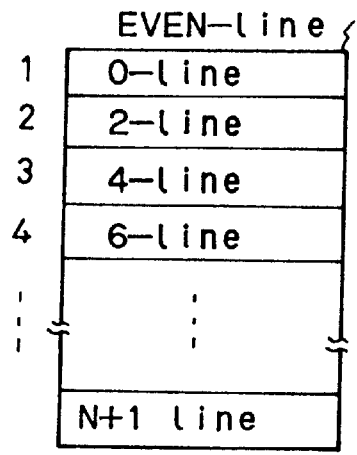
Figure 2:
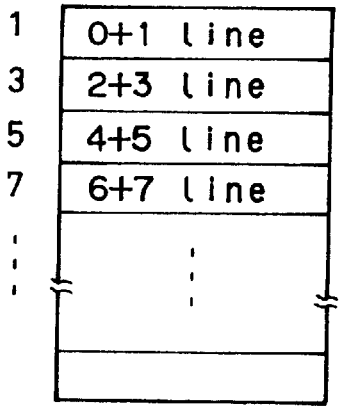
Figure 2:
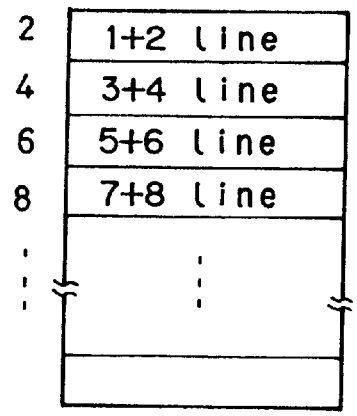

FIG. 2 shows the content of still image data formed in a circuit from the foregoing CCD 12 to the mixing circuit 26. As shown in FIG. 2(A), horizontal lines from 0-line to N-line are provided correspondingly to a number of scanning lines in the CCD 12, and the structure is arranged so that the pixel data of these horizontal lines are transferred to a transfer line for reading out. The data of odd lines (1, 3, 5 . . . line) in the foregoing CCD 12 are stored in the first memory 23 (and the third memory 25) in FIG. 2(B), and the data of even lines (2, 4, 6 . . . line) are stored in the second memory 24 in FIG. 2(C).

The data of these memories 25 and 24 are pixel-mixed between lines in FIGS. 2(B) and 2(C) by the mixing circuit 26 as described above, and as shown in FIG. 2(D), add operation data of 0-line+1-line, 2-line+3-line, 4-line+5-line . . . are outputted as Odd field data. In a state in which the read line of FIG. 2(C) has been shifted underneath by one line (read out from a position indicated by C1 in the figure), they are pixel-mixed between lines in FIGS. 2(B) and 2(C). As shown in FIG. 2(E), add operation data of 1-line+2-line, 3-line+4-line, 5-line+6-line . . . are outputted as even field data. In this respect, in this example, an odd number and an even number in lines of CCD 12, and an odd number and an even number in fields for interlaced scanning are distinguished by representing them as ODD, EVEN, and Odd, Even respectively.

In FIG. 1, at the subsequent stage of the foregoing mixing circuit 26, there is provided an image switching circuit 28 for switching between a moving image and a still image, and this image switching circuit 28 switches from terminal "a" to terminal "b" by the control of the microcomputer 20 when the foregoing freeze switch 16 is depressed. To this image switching circuit 28, there is connected a digital video processor (DVP) 29, and in this DVP 29, color signal processing using the same pixel mix reading system as before is performed, and for example, a color difference signal or a luminance signal is formed, and control of an image position, enlargement process and the like are performed. In this respect, an automatic gain control, gamma processing circuit and the like are arranged in place in addition although not shown.

At the subsequent stage of this DVP 29, there are provided a fourth memory 30 for storing odd field data, a fifth memory 31 for storing even field data, a switching circuit 32 and a D-A converter 33. More specifically, in the foregoing fourth memory 30, Odd field data, in which the data in FIG. 2(D) have been converted into a color difference signal or the like, are stored, and in the fifth memory 31, Even field data, in which the data in FIG. 2(E) have been converted into a color difference signal or the like, are stored.

On the other hand, in a light source unit for supplying light to a light guide 15 arranged in the foregoing scope 10, there are arranged a diaphragm 35 and a light shielding plate 36 between the foregoing light source 14 and an incident end of the light guide 15. This light shielding plate 36 is constructed to rotate, for example, a semi-circular plate, and a driving circuit 38 is connected to rotationally drive the light shielding plate 36. In this example, this light shielding plate 36 intercepts light only for predetermined $\frac{1}{60}$ second after the foregoing freeze switch 16 is depressed in a field O/E signal of a cycle of each $\frac{1}{60}$ second.

Also, to the foregoing diaphragm 35, a diaphragm control circuit 39 is connected, and to the foregoing lamp 14, a lamp driving circuit 40 is connected. This diaphragm control circuit 39 is adapted to drive the diaphragm 35 on the basis of the luminance signal obtained by the foregoing DVP 29 so as to adjust the quantity of light outputted from the light source 14.

Figure 3:
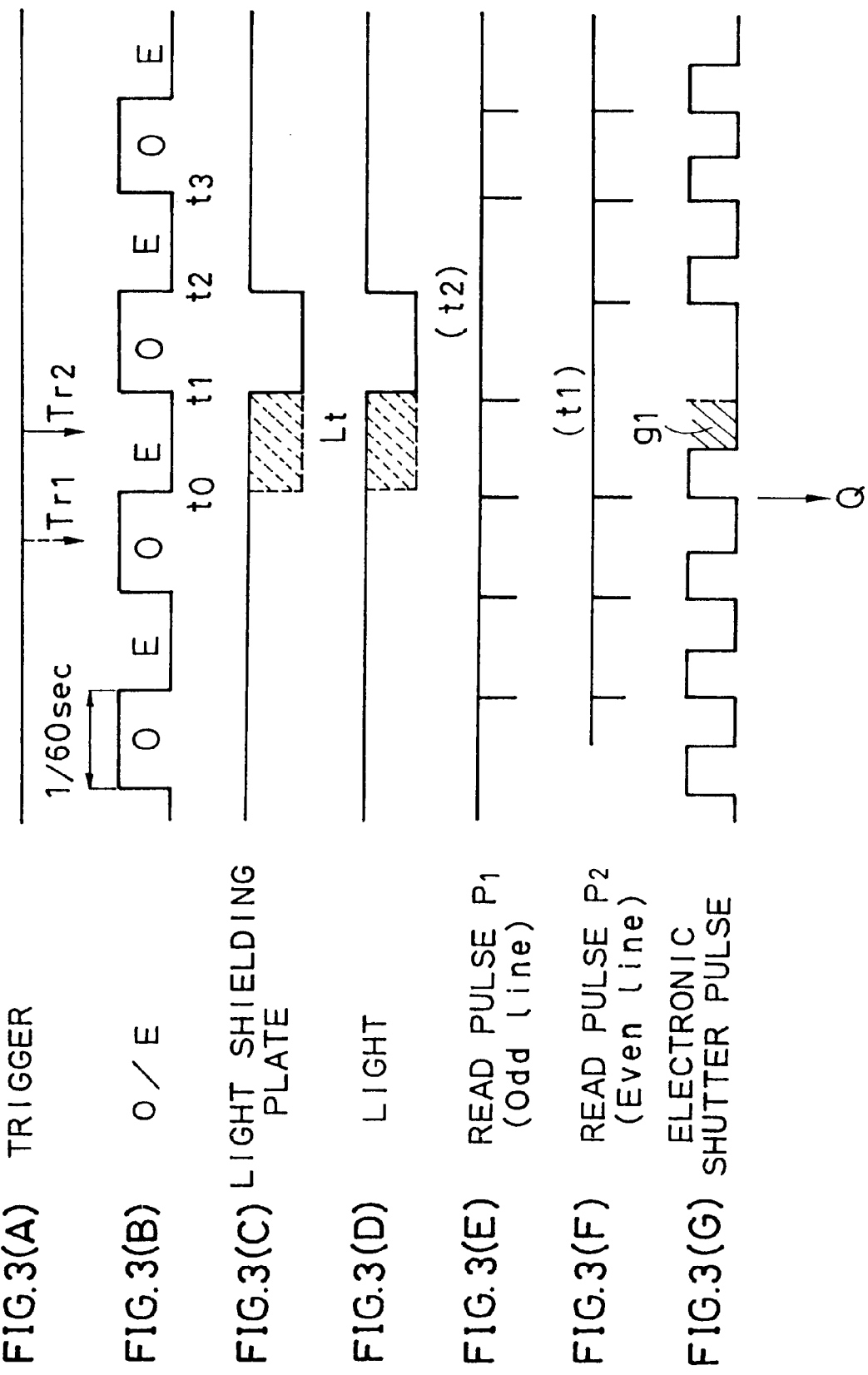
FIGS. 3(A) to 3(G) are explanatory views for illustrating still image formation operation in the first embodiment.
Figure 4:
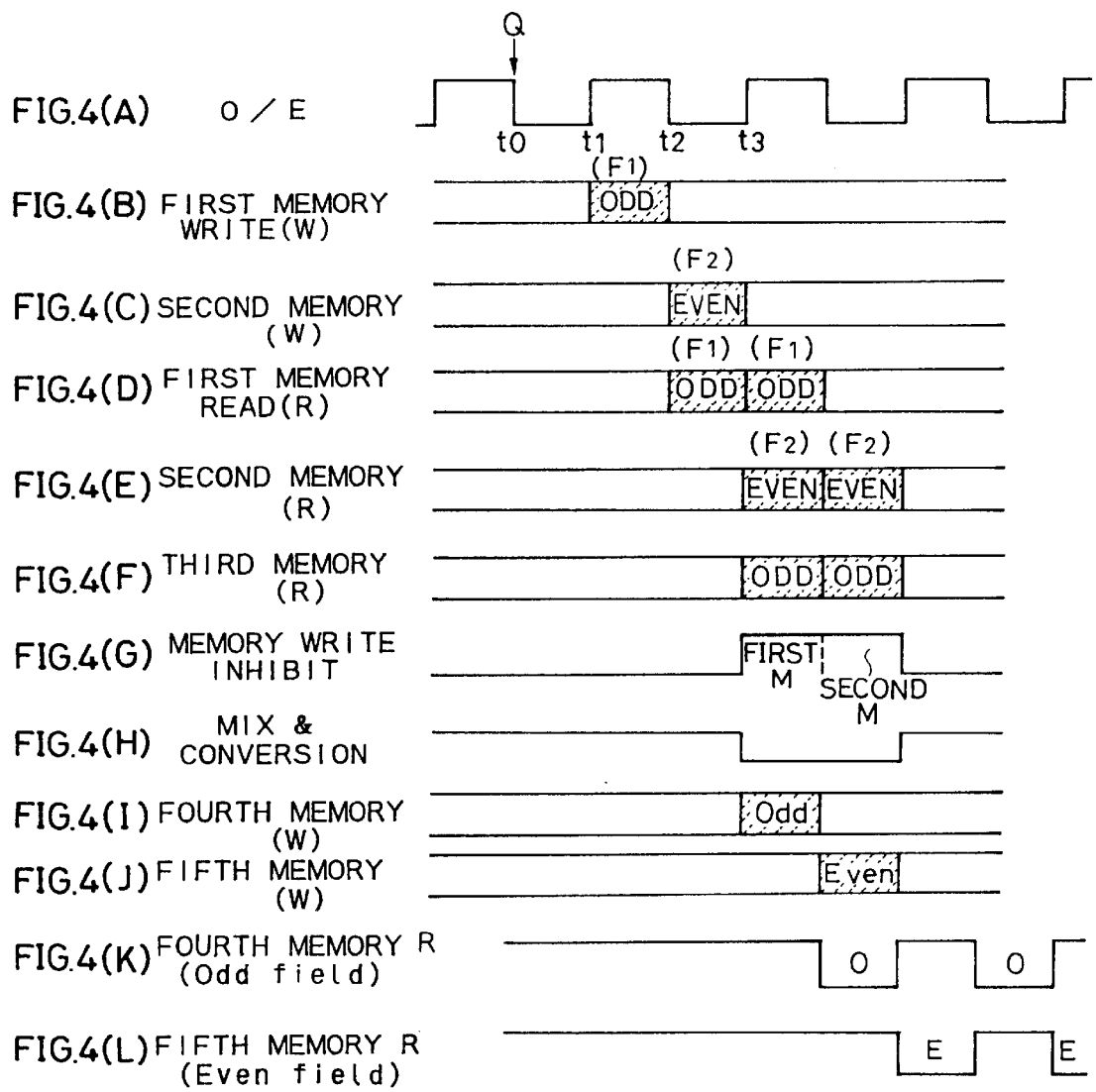
FIGS. 4(A) to 4(I) are explanatory views showing the still image formation operation in the first embodiment, and the follow-up to FIG. 3.

The example is constructed as described above, and the operation will be described with reference to FIGS. 3 and 4 (each figure coincides at point Q temporally). As shown in FIG. 3(B), a timing signal for forming an one-field image in $\frac{1}{60}$ second is used as field O (Odd)/E (Even) signal in the same manner as before. First, under normal conditions, it is set so that moving image processing, that is, the pixel mix reading system at the output of CCD is executed, the light shielding plate 36 in the foregoing FIG. 1 is arranged at a position which does not intersect light, and light from the light source 14 is irradiated from the tip end portion into the object to be observed through the light guide 15.

By this light irradiation, an image for the object to be observed is obtained in the CCD 12 at the tip end portion, and charge corresponding to the image light is accumulated in the CD 12. Pixels between the horizontal lines are added to this accumulated charge through a driving pulse from the CCD driving circuit 18 to be read out, and a pixel mixed signal described in FIG. 1 is outputted. The output signal from this CCD 12 is supplied from an A-D converter 22 to an image switching circuit 28 through a through line L. At this time, the image switching circuit 28 has been switched to terminal "a" side by the microcomputer 20 so that the CCD output signal is supplied to DVP 29. The following operation of the DVP 29 is similar to the conventional one, and a moving image is displayed on a monitor on the basis of the odd field signal stored in the fourth memory 30 and the even field signal stored in the fifth memory 31.

On the other hand, when the freeze switch 16 of the scope 10 has been depressed, the foregoing pixel mix reading system is switched to the all-pixel reading system for still images by the microcomputer 20. For example, when it is assumed that trigger Tr1 (or Tr2) due to the freeze switch 16 is given as shown in FIG. 3(A), the foregoing light shielding plate 36 obstructs the optical path only for $\frac{1}{60}$ second after rise (t1) of the next O/E signal as shown in FIG. 3(C), during the period of which the light is intercepted (FIG. 3 (D)). Accordingly, image data, whose all pixels are read out, become charge accumulated in CCD 12 by exposure Lt during the immediately preceding period of $\frac{1}{60}$ second to the period of time during which the light has been intercepted. This charge has been obtained by an electronic shutter pulse g1 in FIG. 3(G), and the charge (data) of these all pixels are read out by a CCD driving circuit 18.

More specifically, FIG. 3(E) is a read pulse P1 on the ODD line shown in FIG. 2(B), FIG. 3(F) is a read pulse P2 on the EVEN line shown in FIG. 2(C), and through the read pulse P1 having a pulse at time t2 is left out and the read pulse P2 having a pulse at time t1 is left out as shown, the ODD line data and EVEN line data can be successively read out from the CCD 12. Accordingly, the ODD line is read out during the foregoing light shielding period (t1 and t2), and the EVEN line is read out during the next period (t2 to t3). In this respect, there exists no pulse during a period of the foregoing t1 to t2 even in the electronic shutter pulse as shown in FIG. 3(G).

The foregoing ODD line data are written in the first memory 23 as shown in FIG. 4(B), and the EVEN line data are written in the second memory 24 as shown in FIG. 4(C) under the control of the microcomputer 20. Next, as shown in FIGS. 4(D) and 4(E), the ODD line data of the first memory 23 and the EVEN line data of the second memory 24 are read out twice each respectively, and the ODD line data are stored in the third memory 25 in order to adjust the phase of $\frac{1}{60}$ second. Accordingly, as understood from FIGS. 4(E) and 4(F), the data for the ODD line and those for the EVEN line are to coincide in phase (timing).

Each data read out from the foregoing memories 25 and 24 in this way is pixel-mixed by the mixing circuit 26, and in order to enable this pixel mixing to be performed in this example, the first memory 23 and the second memory 24 are write-inhibited as shown in FIG. 4(G). In the same period as this, the pixels are mixed and converted (FIG.4(H)(, and added data of 0-line+1-line, 2-line+3-line, 4-line+5-line . . . shown in FIG. 2(D) are first outputted, and are stored in the fourth memory 30 as the Odd field data (FIG. 4(I)(. Next, added data of 1-line+2-line, 3-line+4-line, 5-line+6-line . . . shown in FIG. 2(E) are outputted, and are stored in the fifth memory 31 as the Even field data.

The moment when these Odd field data and Even field data are read out, a switching circuit 32 selects the fourth memory 30 and the fifth memory 31 so that each field data is alternately outputted as shown in FIGS. 4(K) and 4(L). These field data are outputted to the monitor through a D-A converter 33, and are image-displayed on the monitor through interlaced scanning. As a result, as regards still images, the images will be displayed on the basis of the all pixel data obtained during the same exposure, and images with high image-quality can be obtained. Therefore, even if there is any shake of the endoscope itself in $\frac{1}{60}$ second or any movement of the object to be observed, it becomes possible to observe a sharp still image less affected by it.

In the foregoing embodiment, it is possible to use the electronic shutter function in response to the lightness within the object to be observed as described above, and according to the present invention, the effect of the electronic shutter function is further increased. More specifically, in the conventional system, since an image is formed on the basis of video signals obtained by two exposures, if there is any movement or shake between two exposures, it affects the image quality. According to the present invention, however, a still image is formed on the basis of a video signal obtained by one exposure, and therefore, the effect of shortened signal accumulation time during this one exposure time is directly exhibited and the improved image quality remarkably appears.

In this example, the structure is arranged so that a period for reading out all pixels which form a still image is an one-frame forming period (which is $\frac{1}{30}$ second, and this may be a period for several frames) and thereafter the still image is immediately switched to a moving image signal by the foregoing image switching circuit 28, and therefore, there is an advantage that diaphragm control to make the lightness of the screen constant functions satisfactorily. More specifically, in the foregoing diaphragm control circuit 39, the quantity of light is adjusted on the basis of a luminance signal formed by the DVP 29, and in a case where the still image has been returned to a moving image after the still image operation for a long term, the quantity of light is controlled on the basis of data of the distant past to cause a halation or a dark screen conversely. In this example, however, since the signal is immediately switched to a moving image signal after an one-frame period, such a problem as described above becomes insignificant, and there is an advantage that it is possible to obtain an image having stable lightness.

Further, the present invention has also an advantage that all pixels can be read out without changing the structure of the foregoing CCD 12 and the clock rate. More specifically, it has also conventionally been proposed to read out all pixels within a $\frac{1}{60}$ second period successively (irrespective of an odd line or an even line) using double transfer frequency. In this case, however, since the structure of the transfer line (vertical CCD) of the foregoing CCD 1 must be formed at double densities, there are inconveniences that the structure becomes complicated and yet, the clock rate becomes double among others. The present invention has the advantage that all pixels can be read out without adopting such structure.

As described above, according to the first embodiment, a moving image is formed using the pixel mix reading system, and a still image is formed using the all-pixel reading system, and therefore, it is possible to obtain a smooth image which faithfully reproduces the movement, for the moving image, and on the other hand, a non-blurred image with high image-quality for the still image. Also, as regards the still image, it becomes possible to obtain an effect of shortened accumulation time by the electronic shutter, and further to read out all pixels without changing the structure of the CCD and the clock rate.

Second Embodiment

Figure 5:
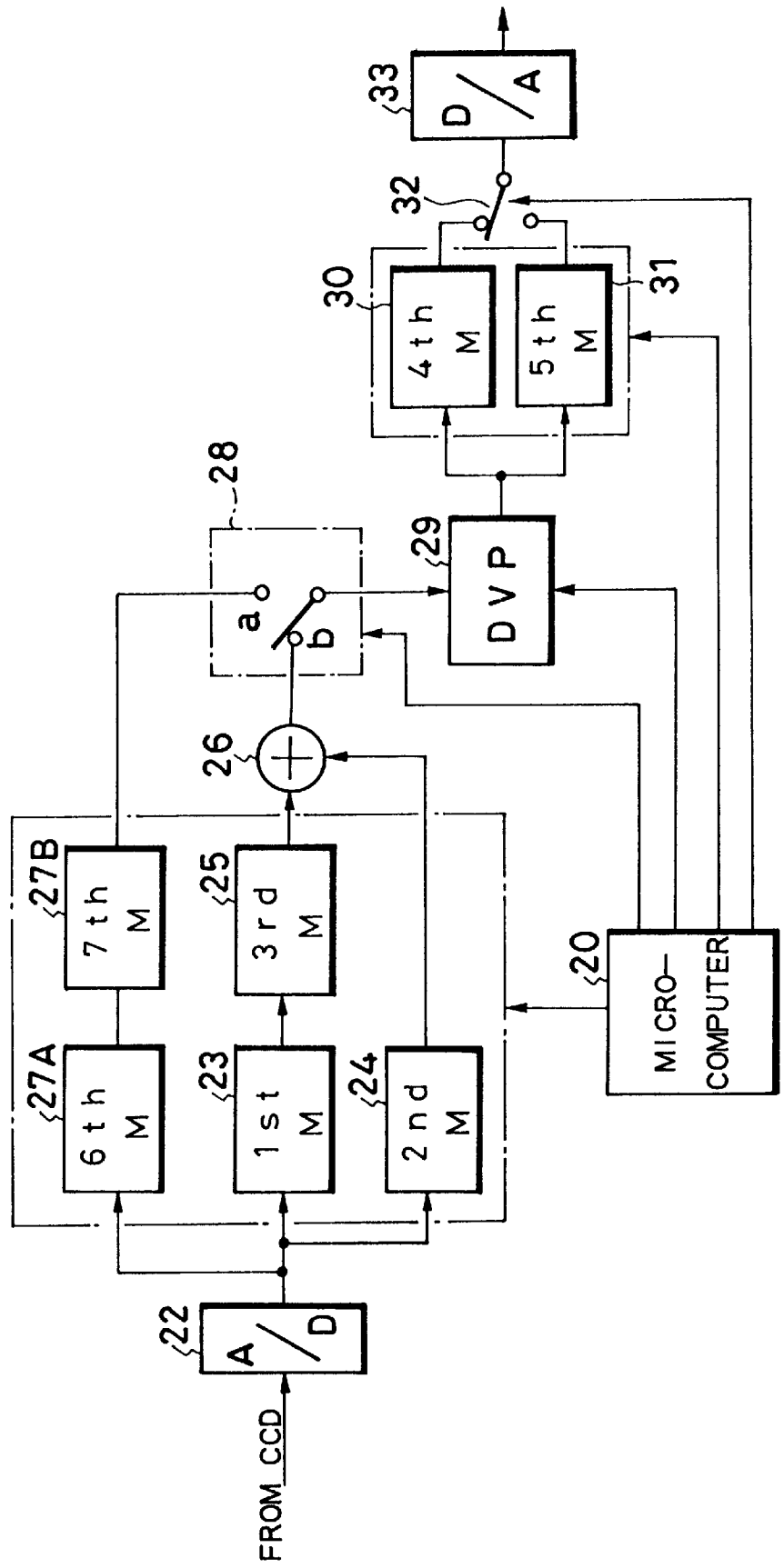
FIG. 5 is a block diagram showing the structure of a part of an electronic endoscope apparatus according to a second embodiment of the present invention.

FIG. 5 shows the structure of a part of an electronic endoscope apparatus according to the second embodiment, and this second embodiment prevents an incomplete image from being displayed using a delay memory. FIG. 5 shows the structure of an A-D converter 22 to a D-A converter 33, and the other structure is the same as in FIG. 1. As in the case of FIG. 1, there are provided an A-D converter for inputting an output signal from CCD 12, memories 23, 24 and 25, a mixing circuit for still images 26, and an image switching circuit 28, and in addition, to the other output line of the foregoing A-D converter 22, there are connected a sixth memory 27A and a seventh memory 27B as a delay memory for the moving image data. More specifically, in this example, so as to prevent an incomplete moving image from being formed through still image data obtained at CCD 12 by means of a light shielding operation, the moving image data are delayed by an amount corresponding to one frame (two fields), or by 1/30 second in terms of time in the foregoing two memories 27A and 27B. Thus, at a timing at which the foregoing incomplete still image data are displayed as a moving image, the moving image is switched to the still image and the still image is displayed, thus avoiding the display of an incomplete moving image.

The foregoing seventh memory 27B and the foregoing mixing circuit 26 are connected to an image switching circuit 28 for switching between a moving image and a still image, and when the foregoing freeze switch 16 is depressed, the image switching circuit 28 switches from terminal "a" to terminal "b" by the control of the microcomputer 20. This image switching circuit 28 is provided, as in the case of FIG. 1, with a digital video processor 29, a fourth memory 30, a fifth memory 31, a switching circuit 32 and a D-A converter 33. Further, in the light source unit, there is arranged a light shielding plate 36 shown in FIG. 1, which intercepts the light only for predetermined 1/60 second after the foregoing freeze switch 16 is depressed.

The second embodiment has the structure described above, and the operation will be described with reference to FIGS. 6 and 7. First, even in this example, the operations described in the foregoing FIGS. 3 and 4 are performed, and a moving image process is executed under normal conditions. When the freeze switch 16 of the scope 10 in FIG. 1 is depressed, the microcomputer 20 causes the foregoing image switching circuit 28 to switch to a terminal "b" side, whereby the process of the all-pixel reading system described in FIGS. 3 and 4 is performed. As a result, as regards the still image, the image is displayed on the basis of the all pixel data obtained during the same exposure, and even if there is any shake of the endoscope itself in 1/60 second or any movement of the object to be observed, it becomes possible to observe a sharp still image less affected by it.

In such a still image process, the still image is delayed by an amount corresponding to one frame for displaying when compared with a moving image because all the pixel data are read out during a two-field period while the light is intercepted during an one-field period. Accordingly, in a case where the moving image data are used as they are without using the delay memory (27A, 27B) of FIG. 5, there is inconvenience that a moving image is displayed through incomplete still image data immediately before switching to the still image.

Figure 6:
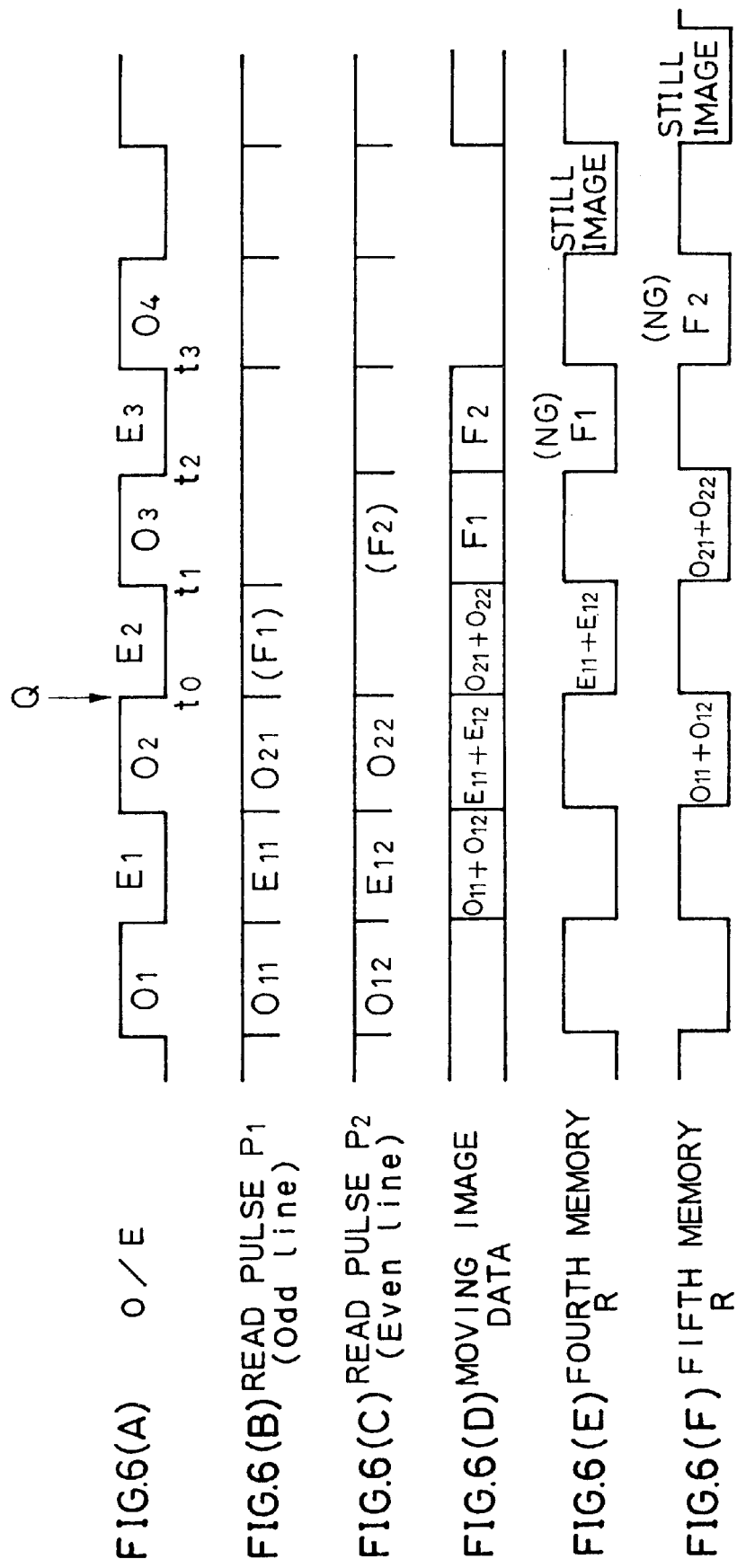
FIGS. 6(A) to 6(F) are explanatory views showing a moving image formation operation when no delay memory is provided in the second embodiment.

FIG. 6 shows a state of such a moving image process. For example, in a case where odd line data O11 and even line data O12, which are shown in FIGS. 6(B) and 6(C), have been obtained during an O1 (O/E signal) period shown in FIG. 6(A), the moving image data outputted from CCD 12 become O11+O12 as shown in FIG. 6(D), these data are stored in the fifth memory 31, are read out and supplied to the monitor during the period shown in FIG. 6(F). Even in the E1 and O2 periods in FIG. 6(A), data of E11+E12 and O21+O22 are outputted on the monitor in the same manner.

However, during the next E2 (t0 to t1) and O3 (t1 to t2) periods in FIG. 6(A), since the light is intercepted and all pixels are read out during this O3 period, only ODD line data F1 is obtained during the foregoing E2 period, and only EVEN line data F2 is obtained during the foregoing E3 period as shown in FIGS. 6(B) and 6(C). Thus, these data F1 and F2 are used also as moving image field data immediately before the still image is displayed as shown in FIGS. 6(D) to 6(F). These data F1 and F2 are unfinished data half the normal field data (luminance and the like), and the moving image at this time does not hold as an image.

Thus, in this example, the sixth memory 27A and the seventh memory 27B are arranged, and the moving image data are delayed by a processing period corresponding to one frame so as to prevent the foregoing data F1 and F2 from being used as the moving image. This processing state is shown in FIG. 7. In this respect, when this moving image is formed, the foregoing image switching circuit 28 is switched to terminal "a" side, and the image signal is subjected to a predetermined. process by DVP 29 as in the case of the still image. Thereafter, the EVEN field data are stored in the fourth memory 30 at the subsequent stage, and the ODD field data are stored in the fifth memory 31.

Figure 7:
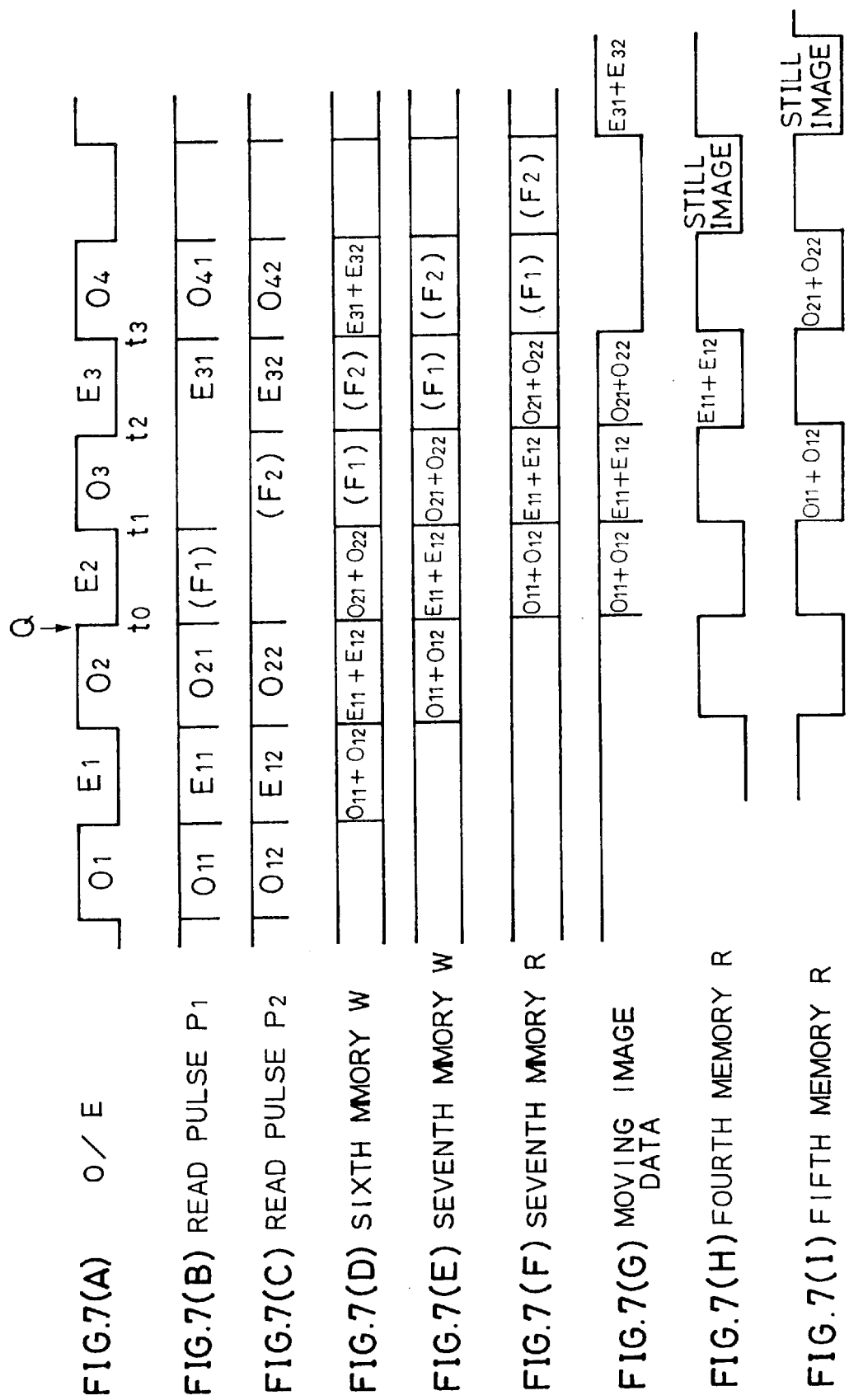
FIGS. 7(A) to 7(I) are explanatory views for illustrating a moving image formation operation in the second embodiment.

In FIG. 7, odd line data O11 (FIG. 7(B)( and even line data O12 (FIG. 7(C) ( which have been obtained during an O1 (O/E signal) period in FIG. 7(A) are delayed by an amount corresponding to one field (1/60 second) by the sixth memory 27A as shown in FIG. 7(D), and are further delayed by an amount corresponding to one field by the seventh memory 27B as shown in FIG. 7(E). Accordingly, O11+O12, which are read out from the seventh memory 27B (FIG. 7(F)( and become moving image data, are delayed temporally by time corresponding to one frame (1/30 second) when compared with the case of FIG. 6. The same is applicable to E11+E12 and O21+O22 which can be obtained during the next E2 and O3 periods, and all the moving data are displayed by time corresponding to one frame.

Therefore, as shown in FIG. 7(H), the foregoing E11+E12 are used during a period (E3) in which still image data F1 have been extracted in FIG. 6, and as shown in FIG. 7(I), the foregoing O21+O22 are used during a period (O3) in which still image data F2 have been extracted in FIG. 6. As a result, the still image data F1 and F2 will not be used as moving image data to avoid incomplete display of moving images.

In the foregoing second embodiment, the memories 27a and 27B have been used as delay means, but another delay means may be used. Also, in the foregoing example, the delay time has been set to time corresponding to one frame, but in the case of processing at different timing, it may be set to time corresponding to one field, to three fields, to two frames or the like.

Third Embodiment

The structure of this third embodiment is the same as that of the electronic endoscope apparatus shown in FIG. 1, and the third embodiment prevents any incomplete image from being displayed by controlling the fourth and fifth memories 30 and 31 so as to write-inhibit them in a predetermined period by the use of the microcomputer 20.

As described in the second embodiment, the all-pixel reading system for still images is executed by depressing the freeze switch 16 of the scope 10 in FIG. 1. In this still image processing, since all pixel data are read out during a two-field period while the light is shielded during a one-field period, the still image is displayed by time corresponding to one frame for displaying when compared with the moving image, and the moving image is displayed through an incomplete still image data immediately before switched to the still image.

Figure 8:
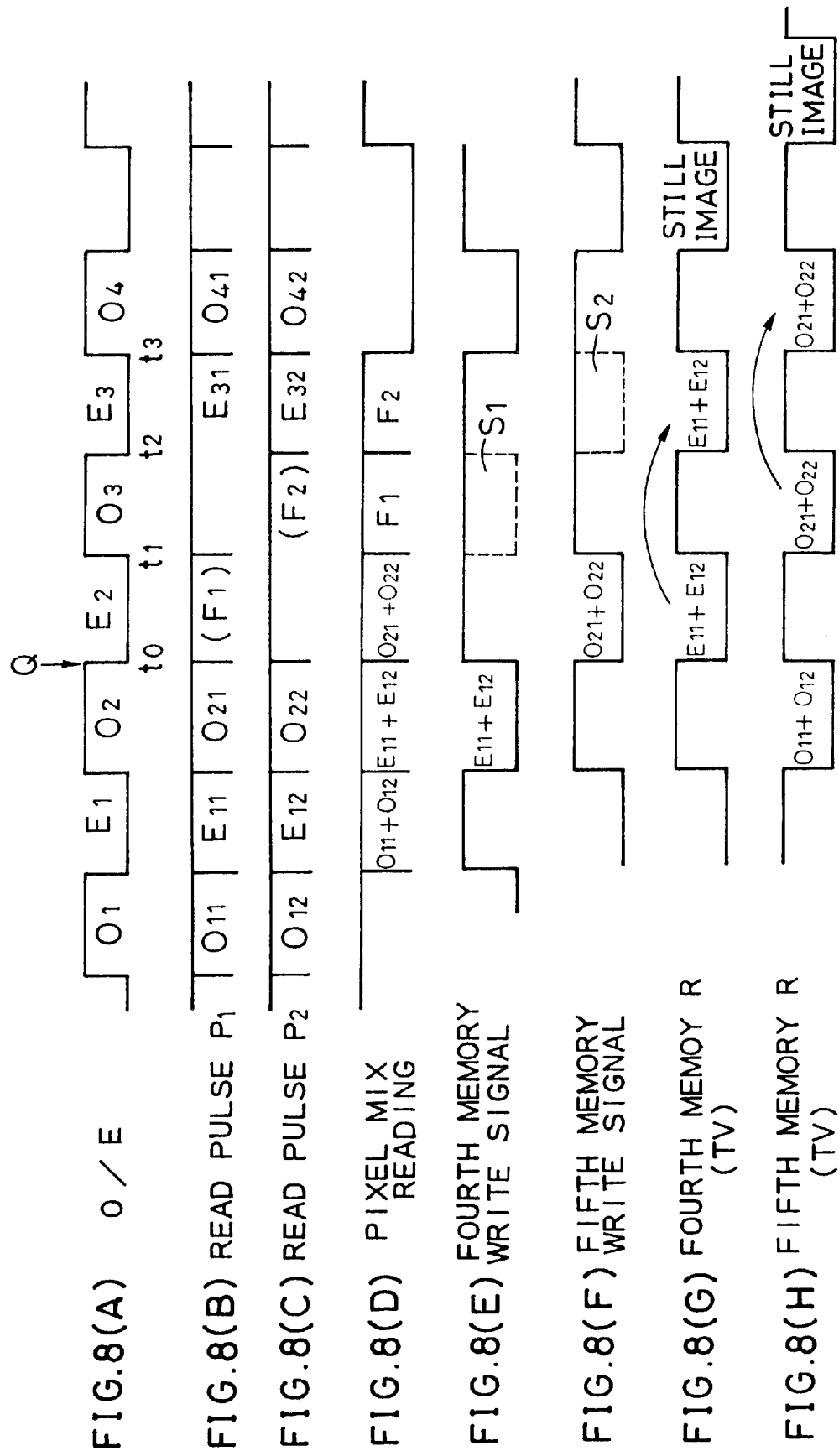
FIGS. 8(A) to 8(H) are explanatory views for illustrating a moving image formation operation in the third embodiment.

Thus, in this third embodiment, a write-inhibit signal is outputted to a memory for storing the moving image data, whereby the foregoing data F1 and F2 corresponding to, for example, one frame are prevented from being used as the moving image, and this processing state is shown in FIG. 8. More specifically, odd line data O11 (FIG. 8(B)( and even line data O12 (FIG. 8(C)(, which have been obtained during the O1 (O/E signal) period of FIG. 8(A), are subjected to the pixel mix reading by CCD 12 as shown in FIG. 8(D), and image signals are formed on the basis of these signals. In a write signal for the fourth memory 30 at the subsequent stage, a write-inhibit period S1 shown in FIG. 8(E) is set, in a write signal for the fifth memory 31, a write-inhibit period S2 shown in FIG. 8(F) is set, and unfinished still image data F1 and F2 will not be written in the foregoing fourth memory 30 and fifth memory 31.

Then, as shown in FIG. 8(G), data of E11+E12 are read out twice from the fourth memory 30, and data of O21+O22 are also read out twice from the fifth memory 31. Accordingly, in FIG. 6, the foregoing data of E11+E12 are used during a period (E3), in which the still image data F1 has been extracted, and the foregoing data of O21+O22 are used during a period (O3), in which the still image data F2 has been extracted. As a result, the still image data F1 and F2 will not be used as the moving image data to thereby avoid the display of any incomplete moving images. In the foregoing third embodiment, the write-inhibit period has become equal to time corresponding to one frame in total, but in the case of processing at different timing, the write-inhibit period will be appropriately set in response thereto.

Fourth Embodiment

The structure of this fourth embodiment is also the same as that of the electronic endoscope apparatus shown in FIG. 1, and prevents the display of any incomplete image and eliminates the blurred screen by the control of the fourth and fifth memories 30 and 31 by the microcomputer 20. This fourth embodiment also performs the foregoing moving image process, the still image process described in FIGS. 3 and 4, and the process shown in FIGS. 9 and 10.

Figure 9:
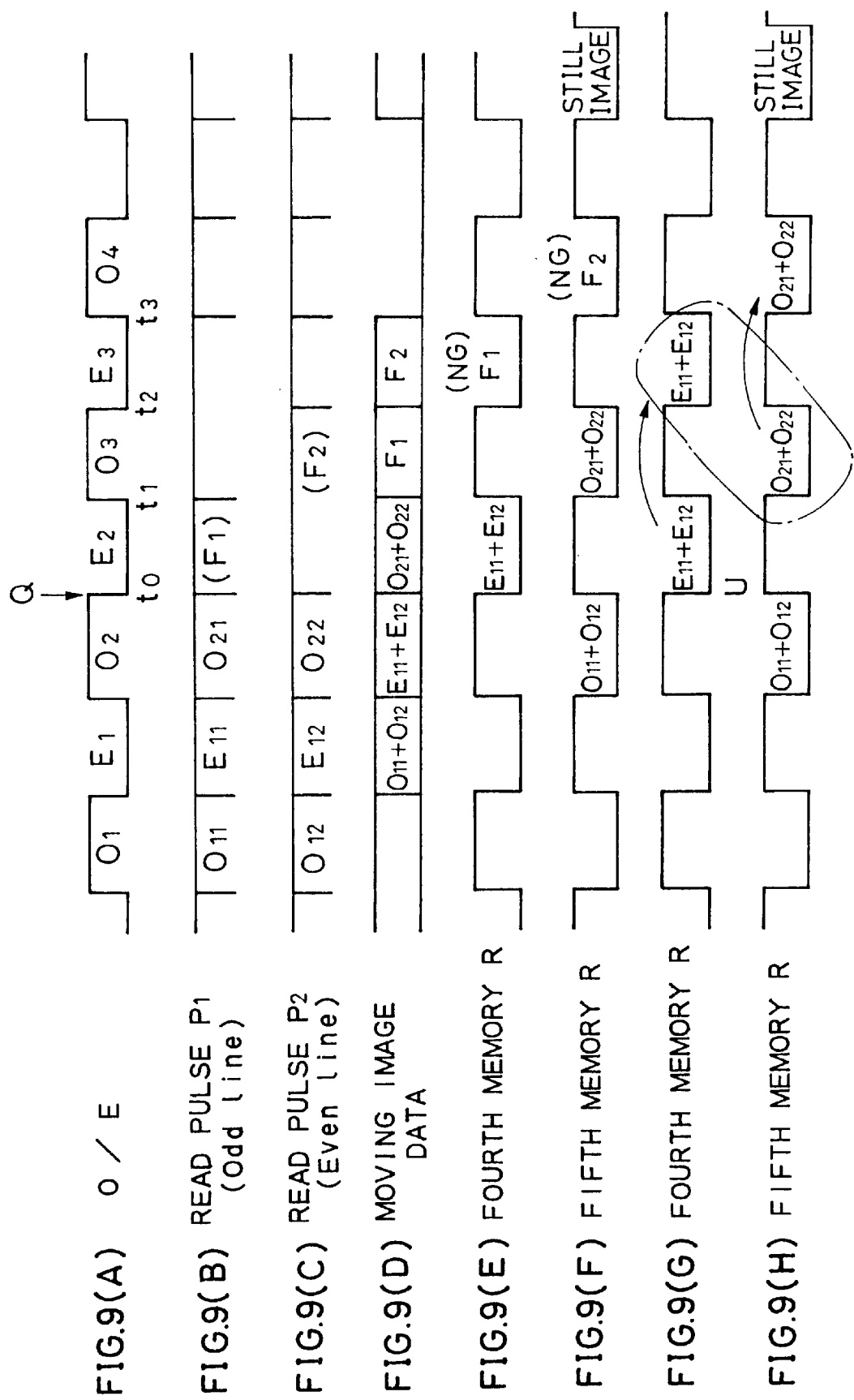
FIGS. 9(A) to 9(H) are explanatory views for illustrating a moving image formation operation in which inconvenience occurs in a certain condition in the fourth embodiment.

In FIG. 9, when it is assumed that signals of O11+O12 shown in FIG. 9(D) have been obtained as in the case of FIG. 8, these signals are stored in the fifth memory 31, and during a period shown in FIG. 9(F), are read out to be supplied to the monitor. Even during periods of E1 and O2 in FIG. 9(A), the data of E11+E12 and O21+O22 are likewise outputted on the monitor.

Since, however, during periods of the next E2 (t0 to t1) and O3 (t1 to t2) in FIG. 9(A), the light is intercepted and all pixels are read out during this O3 period, only the ODD line data F1 can be obtained during the foregoing E2 period, and only the EVEN line data F2 can be obtained during the foregoing O3 period as shown in FIGS. 9(B) and 9(C). These data F1 and F2 are also used as field data for moving images immediately before still images are displayed as shown in FIGS. 9(D) to 9(F). These data F1 and F2 are unfinished data half the normal field data (luminance and the like), and the moving image at this time does not hold as an image.

Figure 10:
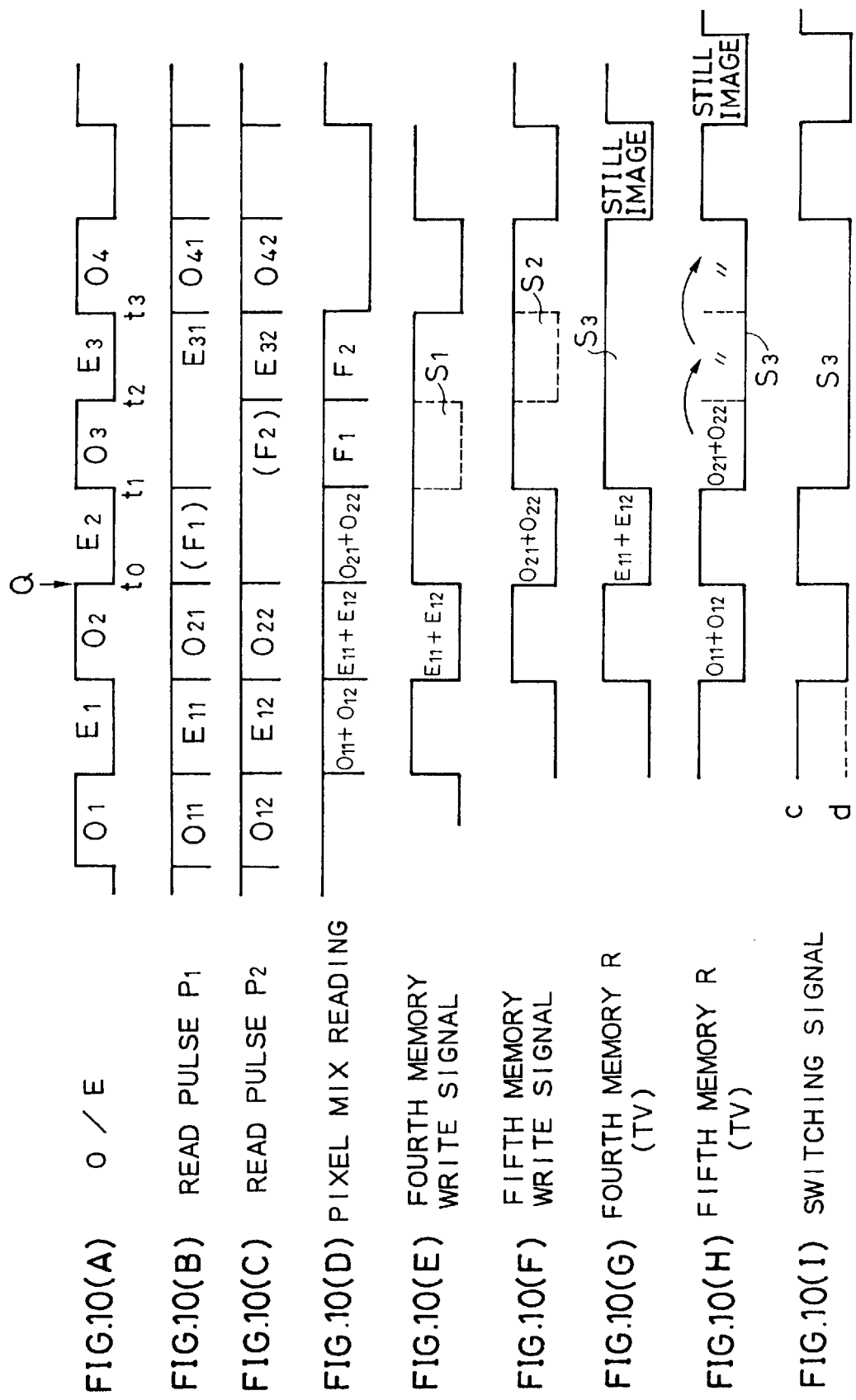
FIGS. 10(A) to 10(I) are explanatory views for illustrating a moving image formation operation in the fourth embodiment.

Thus, even in the fourth embodiment, a write-inhibit signal is outputted to the memories 30 and 31, in which moving image data are stored, as shown in FIG. 10 so as to prevent the foregoing data F1 and F2 corresponding to one frame from being used as moving images. More specifically, the pixel mix reading is performed from CCD 12 as shown in FIGS. 10(A) to 10(D). In a write signal for the fourth memory 30, a write-inhibit period S1 shown in FIG. 10(E) is set, in a write signal for the fifth memory 31, a write-inhibit period S2 shown in FIG. 10(F) is set, and unfinished still image data F1 and F2 will not be written in the foregoing fourth memory 30 and fifth memory 31.

When performed as described above, the same data are normally read out twice from each memory 30, 31, and the data shown in FIGS. 9(G) and 9(H) are obtained. More specifically, as shown in FIG. 9(G), the data of E11+E12 are read out-twice from the fourth memory 30, the data of O21+O22 are also read out twice from the fifth memory 31 and the foregoing data of E11+E12 are used during a period (E3) in which the still image data F1 has been read out in FIG. 9(E). Also, the foregoing data of O21+O22 are used during a period (O3) in which the still image data F2 has been read out in FIG. 9(F). Accordingly, the still image data F1 and F2 are not used as moving image data to thereby avoid the display of any incomplete moving images.

In the foregoing reading process, however, on focusing attention on U portion in FIGS. 9(G) and 9(H), the data of O21+O22, which have been obtained temporally later (1/60 second later) than the data of E11+E12, are previously read out and displayed, and if the object to be observed or the endoscope itself is moved, the screen (image) will be blurred.

Thus, in this example, only data of either odd field or even field will be used again as shown in FIGS. 10(G) to 10(I). More specifically, as shown in FIG. 10(G), a read signal, which is not read out only during a predetermined three-field period S3, is given to the fourth memory 30, and a read signal, which reads out during the same three-field period S3, is given to the fifth memory 31. Simultaneously, a switching signal for selecting the fifth memory 31 (terminal "d") during the foregoing three-field period S3 is supplied to the switching circuit 32 at the subsequent stage as shown in FIG. 10(I).

Then, the data of O21+O22 are read out three times continuously as shown in FIG. 10(H), and these data are outputted from the switching circuit 32 to the monitor through the D-A converter 33. As a result, the moving image for the last one frame immediately before switched to the still image is to be displayed through only the foregoing data of O21+O22 to thereby prevent the blurred image caused through the data which are temporally inverted.

In the foregoing fourth embodiment, the write-inhibit period became equal to time corresponding to one frame in total, and continuous reading of odd field data became equal to time corresponding to three fields, but in the case of processing at different timing, the write-inhibit period and continuous reading period will be appropriately set in response thereto. Also, the data to be continuously read out may be even field data.

Fifth Embodiment

Figure 11:
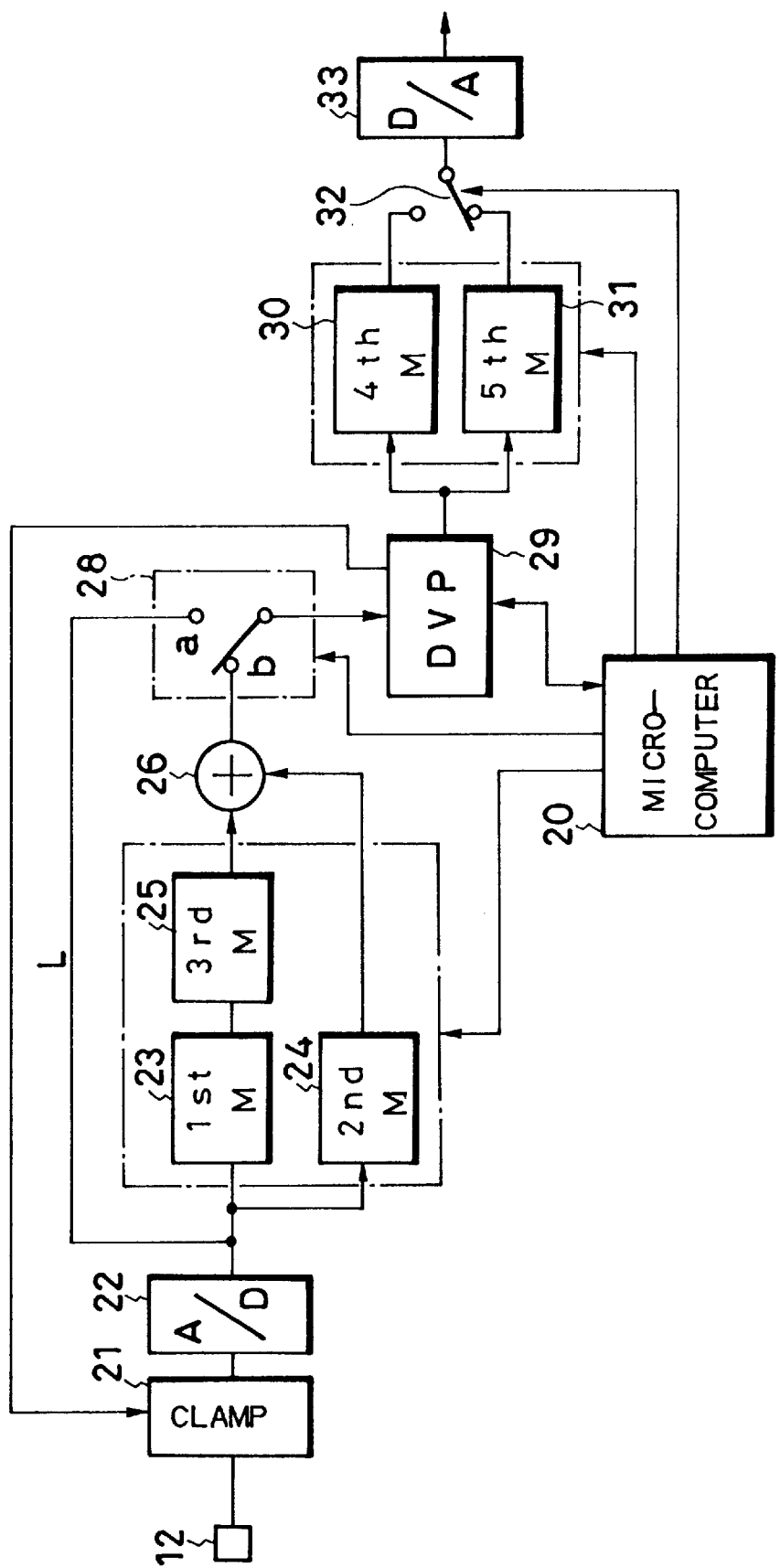
FIG. 11 is a block diagram showing the structure of a part of an electronic endoscope apparatus according to a fifth embodiment.

FIG. 11 shows the structure of a part of an electronic endoscope apparatus according to the fifth embodiment. This fifth embodiment stabilizes a black level clamping process when the still image is selected, and prevents the color reproducibility from being deteriorated. In FIG. 11, the other structure which is not shown is the same as in FIG. 1, but there is provided a clamping circuit 21 for inputting an output signal from CCD 12 to perform a clamping process for controlling the black level constant. This clamping circuit 21 is provided together with a correlating double sampling circuit, an automatic gain circuit and the like. To the subsequent stage of the clamping circuit 21, there are connected, through the A-D converter 22, the foregoing first memory 23, a second memory 24, a third memory 25, a still image mixing circuit 26, an image switching circuit 28 and a digital video processor (DVP) 29. This DVP 29 processes the foregoing signal, and transmits a clamp signal to the foregoing clamping circuit 21. More specifically, this DVP 29 gives an optical black pulse (OBP) to a video signal to extract voltage for an optical black period (black setting period), and forms a clamp signal for controlling the black level constant. This clamp signal is fed back to the foregoing clamping circuit 21.

In such a clamping process, even in a case where a still image signal is selected at terminal "b" through the switching control of the foregoing image switching circuit 28 by the foregoing microcomputer 20 in this example, concerning the black level, the terminal "b" is instantaneously switched to terminal "a" to extract the voltage during the optical black period for a moving image signal. Even when the still image has been displayed for many hours, stable control of the black level is performed in consideration of the conditions at this point in time, and it becomes possible to secure good color reproducibility. At the subsequent stage of the foregoing DVP 29, there are provided a fourth memory 30, a fifth memory 31, a switching circuit 32 and a D-A converter 33.

This fifth embodiment has the foregoing structure, and in this case, similar moving image and still image processing to the foregoing each example is performed, and the clamping process is executed as shown in FIGS. 12 and 13. FIG. 12 shows the operation when the moving image is selected. In this clamping process, an optical black pulse (OBP) shown in FIG. 12(B) is given to a moving image signal (video signal) for each horizontal scanning period (H) shown in FIG. 12(A) by the foregoing DVP 29, whereby voltage (black level voltage) of the optical black period (portion in which the incident light is shielded) K of a moving image signal is extracted, and a clamp pulse shown in, for example, FIG. 12(C) is formed. This clamp pulse is a signal representing the black level value by its width, and is supplied to the clamping circuit 21 at the previous stage. In this clamping circuit 21, the black level signal of the moving image signal is reproduced through a clamp signal, whereby the black level of the moving signal is controlled to become constant.

In the other still image processing, however, since the same signals stored in the foregoing first memory 23 and second memory 24 are repeatedly used, a clamp signal is formed in accordance with old data of the past after a lapse of a certain time after the display of a still image is terminated, and it is switched to a moving image. At this time, the clamp signal does not match the present condition, and the black level greatly changes. Therefore, in this example, the clamp signal is always controlled so as to be extracted from the moving image signal as described above, and this operation is shown in FIG. 13.

In FIG. 13, the still image signal of FIG. 13(A) is supplied to terminal "b" of the foregoing image switching circuit 28, the moving image signal of FIG. 13(B) is supplied to the other terminal "a," and the switching signal of FIG. 13(C) is given to the switching circuit 28 from the microcomputer 20. This switching signal is formed from the OBP (optical black pulse) shown in FIG. 13(D), the upper side is connected to terminal "b," and the lower side is connected to terminal "a." According to this, the terminal is switched to terminal "a" during a predetermined short period even when the still image (terminal "b") has been selected, whereby the optical black period K of the moving signal is extracted for each 1H.

In the foregoing DVP 29, the OBP of FIG. 13(D) is given to a still image signal in which such one portion of moving image information has been incorporated to form the clamp signal of FIG. 13(E). This clamp signal is fed back to the clamping circuit 21, where a black level signal is reproduced. Therefore, when the still image is switched to the moving image, the control is performed so that the black level becomes constant, and good color reproducibility can be obtained.

In the foregoing fifth embodiment, it has been arranged so that the black level voltage for moving images is extracted by switching the image switching circuit 28, but it may be possible to fetch the moving image signal from a route different from the still image signal when the still image is selected, and to directly extract the black level voltage from this moving image signal.

Sixth Embodiment

Figure 14:
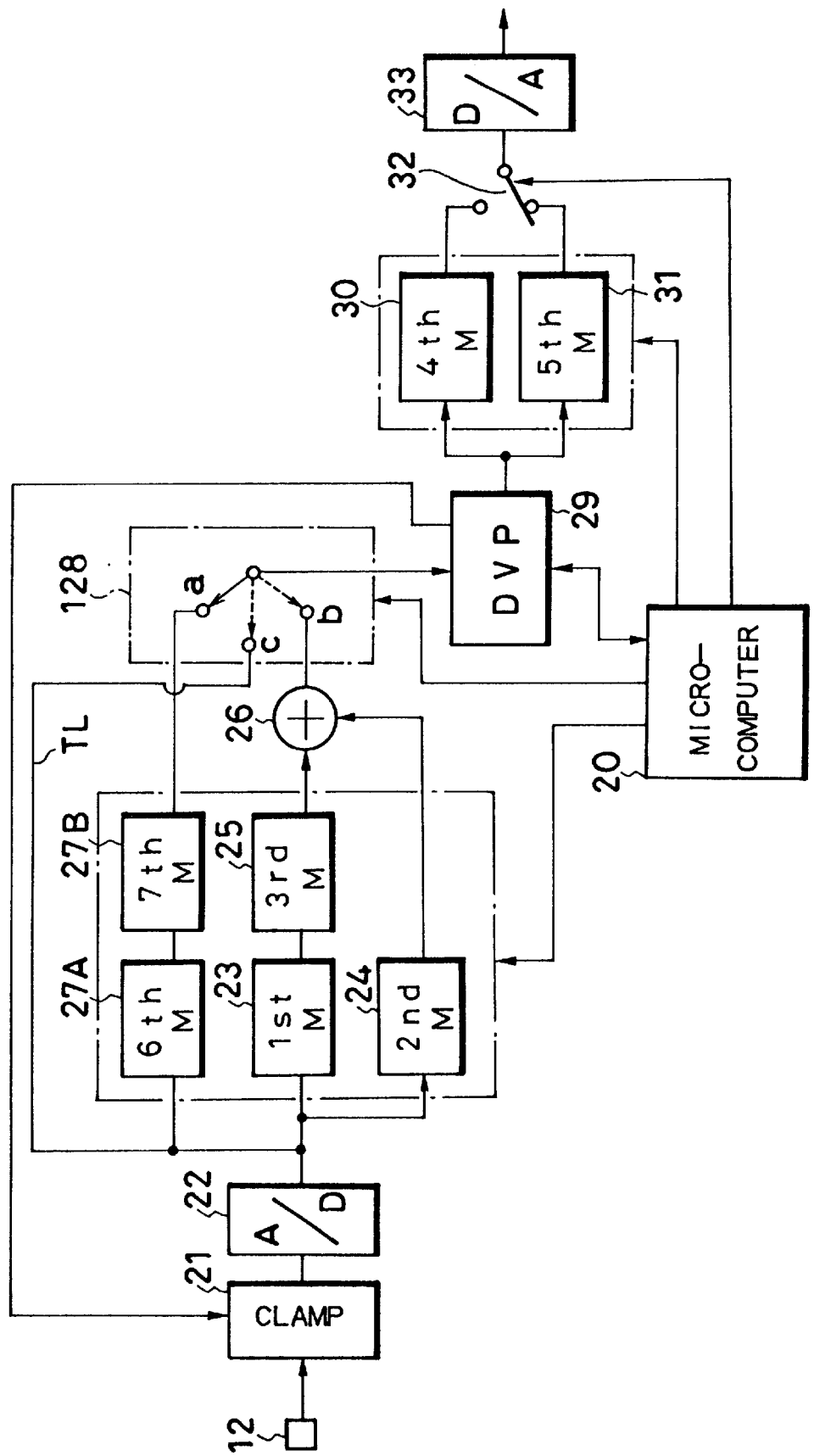
FIG. 14 is a block diagram showing the structure of a part of an electronic endoscope apparatus according to a sixth embodiment.

FIG. 14 shows the structure of a part of an electronic endoscope apparatus according to the sixth embodiment. This sixth embodiment is obtained by improving the black level clamping process in an apparatus according to the second embodiment, and the other structure which is not shown is the same as in FIG. 1. Even in FIG. 14, at the subsequent stage of CCD 12, there is provided a clamping circuit 21 for performing a clamping process to control the black level constant, and at the subsequent stage of this clamping circuit 21, there are provided an A-D converter 22, a first memory 23, a second memory 24, a third memory 25 for phase adjustment, and a still image mixing circuit 26. Also, to the other output line of the foregoing A-D converter 22, there are connected, as a delay memory for moving image data, a sixth memory 27A and a seventh memory 27B. More specifically, in this example, so as to prevent any incomplete moving image from being formed through still image data obtained by CCD 12 by means of a light shielding operation, the moving image data are delayed by an amount corresponding to one frame (two fields) or temporally 1/30 second in the foregoing two memories 27A and 27B.

Further, there is provided an image switching circuit 128 for switching the output (terminals "a" and "b") from the foregoing seventh memory 27B and the foregoing mixing circuit 26, and this image switching circuit 128 switches terminal "a" to terminal "b" by the control of the microcomputer 20 when the foregoing freeze switch 16 is depressed. Also, a moving image signal outputted from the foregoing A-D converter 22 is directly supplied to the terminal "c" of the image switching circuit 128 through a TL line (through line), and the optical black period of this moving image signal is utilized. To this image switching circuit 128, there is connected DVP 29. In this DVP 29, an optical black pulse (OBP) is given to the video signal to extract voltage for the optical black period (black setting period), a clamp signal for controlling the black level constant is formed, and this clamp signal is fed back to the foregoing clamping circuit 21.

In such a clamping process, even in a case where a moving image signal (still image signal at "b") is selected at terminal "a" through the switching control of the foregoing image switching circuit 128 by the foregoing microcomputer 20 in this example, concerning the black level, the terminal "a" is instantaneously switched to terminal "c" to extract the voltage during the optical black period for a moving image signal. Even when the moving image has been displayed by, for example, an amount corresponding to one frame by the memories 27A and 27B, stable control of the black level is performed in consideration of the conditions at this point in time, and it becomes possible to secure good color reproducibility. In this respect, at the subsequent stage of the foregoing DVP 29, there is provided a circuit from the fourth memory 30 and the fifth memory 31 to the D-A converter 33.

Figure 15:
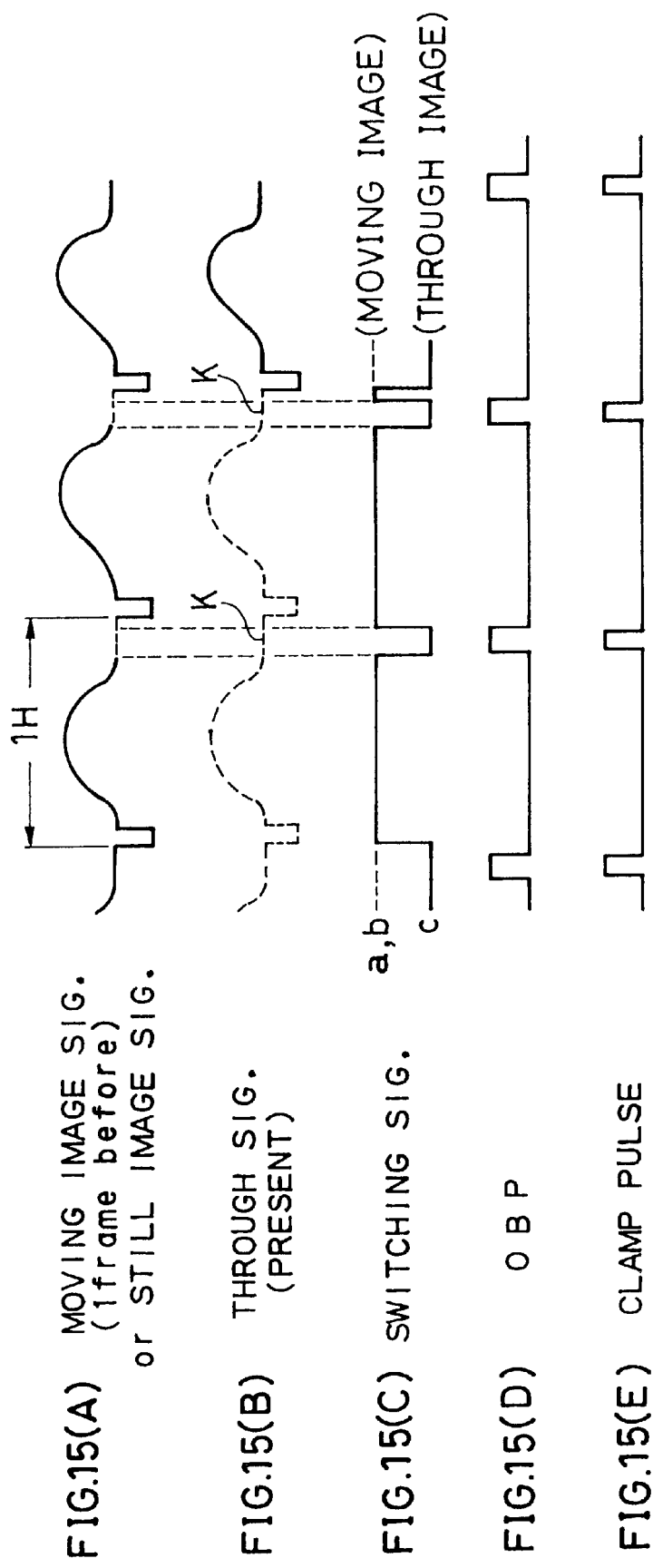
FIGS. 15(A) to 15(E) are waveform views showing a clamping process in the sixth embodiment.

In this example, as described in FIG. 7, the moving image data are delayed by a processing period corresponding to one frame by the foregoing sixth memory 27A and seventh memory 27B so that the data F1 and F2 are not used as the moving image, and therefore, the display of any incomplete moving image is avoided. In this sixth embodiment, however, the moving image data are delayed by an amount corresponding to one frame, and therefore, the clamp signal is to be formed in accordance with data of the past delayed by an amount corresponding to one frame, and the black level greatly changes. Thus, as shown in FIG. 15, the clamp signal is controlled so that it is always extracted from the through moving image signal.

More specifically, the moving image signal in FIG. 15(A) is supplied to terminal "a" of the foregoing image switching circuit 128, the through signal (the moving image signal from the through line TL) in FIG. 15(B) is supplied to terminal "c," and the switching signal in FIG. 15(C) is given to a switching circuit 28 from the microcomputer 20. This switching signal is formed from the OBP (optical black pulse) shown in FIG. 15(D), and the upper side is connected to terminal "a" (or "b"), and the lower side is connected to terminal "c." According to this, even when the moving image (terminal "a") is selected, the optical black period K of the moving image signal at this point in time is extracted for each H by switching to terminal "c" for a predetermined short period.

In the foregoing DVP 29, the OBP of FIG. 15(D) is given to a moving image signal in which the black level period of such a through signal has been incorporated to form a clamp signal of FIG. 15(E). This clamp signal is fed back to the clamping circuit 21, where the black level signal is reproduced. Accordingly, control of the black level is performed with stability, and good color reproducibility can be obtained.

Also, even when the still image has been selected, a signal of the optical black period of the through signal is likewise used. More specifically, even in the still image, since the image is displayed through the same signals stored in the foregoing first memory 23 and second memory 24, a clamp signal is formed in accordance with old data of the past, and when switched to the moving image, the clamp signal does not match the present condition, but the black level greatly changes. Accordingly, even when this still image processing is selected, the signal is switched into the through signal (terminal "c") so as to extract a signal of the optical black period in the same manner as described above, and the black level voltage at this point in time is extracted to thereby control the black level constant.

What is claimed is:

1. An image-pickup device having a plurality of color filters arranged in units of pixels;

light shielding means for intercepting illumination light so that pixel signals for a predetermined period of time are not accumulated on said image-pickup device;

switching means for switching driving control for both a pixel mix reading system, which mixes pixels accumulated on said image-pickup device between upper and lower horizontal lines to output from said image-pickup device, and an all-pixel reading system, which reads out signals of all pixels accumulated on said image-pickup device by one exposure through the use of a light shielding period set by said light shielding means;

an image-pickup device driving circuit for controlling so as to read out, concerning all pixel signals accumulated on said image-pickup device by one exposure, image signals on either odd or even horizontal line first, and next to read out image signals on the remaining horizontal line;

a memory for storing, at the execution of said all-pixel reading system, image signals on said odd horizontal line obtained from said image-pickup device and image signals on said even horizontal line;

a phase adjustment memory for adjusting a phase, at the execution of said all-pixel reading system, between image signals on a predetermined horizontal line previously stored in said memory and image signals on another horizontal line;

a mixing circuit for forming a still image signal by mixing pixel signals of said odd horizontal line and said even horizontal line during the same exposure which have been read out from said memory for storing image signals and said phase adjustment memory; and an image switching circuit for directly inputting a moving image signal of the pixel mix reading system outputted from said image-pickup device to switch either said moving image signal or a still image signal outputted from said mixing circuit on the basis of the operation of a freeze switch.

2. An electronic endoscope apparatus according to claim 1, further comprising:

delay means for delaying moving image data obtained using said pixel mix reading system by a predetermined period of time; and a signal processing circuit for forming a moving image signal on the basis of moving image data obtained through said delay means.

3. An electronic endoscope apparatus according to claim 2, further comprising:

a delay memory for delaying a moving image signal of said pixel mix reading system outputted from said image-pickup device by a processing period corresponding to one frame; and an image switching circuit for switching between a moving image signal outputted from said delay memory and said still image signal on the basis of the operation of a freeze switch.

4. An electronic endoscope apparatus according to claim 1, further comprising:

a memory for storing at least moving image data, wherein said circuit for controlling inhibits still image data, which have been read out from said image-pickup device when said all-pixel reading system is selected, from being written in said memory as moving image data.

5. An electronic endoscope apparatus according to claim 1, further comprising:

a memory for storing at least moving image data, wherein said circuit for controlling sets a write-inhibit period so as to prevent still image data, which have been read out from said image-pickup device when said all-pixel reading system is selected, from being written in said memory as moving image data, and continuously reads out the data of either odd field or even field which have been already written in said memory, as frame data for said write-inhibit period.

6. An electronic endoscope apparatus, comprising: an image-pickup device having a plurality of color filters arranged in units of pixels;

light shielding means for intercepting illumination light so that pixel signals for a predetermined period of time are not accumulated on said image-pickup device;

switching means for switching driving control for both a pixel mix reading system, which mixes pixels accumulated on said image-pickup device between upper and lower horizontal lines to output from said image-pickup device, and an all-pixel reading system, which reads out signals of all pixels accumulated on said image-pickup device by one exposure through the use of a light shielding period set by said light shielding means;

a clamping circuit for clamping an image signal outputted from said image-pickup device through a clamp signal;

switching control means for controlling so as to extract a black information signal in a moving image signal directly outputted from said image-pickup device using said pixel mix reading system even when said all-pixel reading system is selected; and a signal processing circuit for forming a clamp signal from the black information signal obtained by the control of said switching control means to feed back said clamp signal to said clamping circuit.

7. An electronic endoscope apparatus according to claim 6, further comprising delay means for delaying moving image data obtained using said pixel mix reading system by a predetermined period of time, wherein said switching control means directly inputs a moving image signal obtained using said pixel mix reading system without through said delay means to extract the black information signal in said moving image signal.

* * * * *